United States Patent
Diazgranados Bolivar et al.

(10) Patent No.: US 12,220,045 B2
(45) Date of Patent: Feb. 11, 2025

(54) BACKPACK FOR DOMICILIARY MEDICAL SERVICES

(71) Applicant: SEGUROS BOLIVAR S.A., Bogota (CO)

(72) Inventors: Camila Andrea Diazgranados Bolivar, Bogota (CO); Carlos Javier Durango Caicedo, Bogota (CO); Leonardo Andres Gonzalez Gomez, Bogota (CO); Nicolas Manrique Suarez, Bogota (CO); Pablo Munoz Perez, Bogota (CO); Julian Andres Murillo Ramirez, Bogota (CO); Maria Jose Quintero Alvarez, Bogota (CO); Jennifer Anezka Requena Diaz, Bogota (CO); Daniela Botero Ortega, Bogota (CO)

(73) Assignee: SEGUROS BOLIVAR S.A., Bogota (CO)

( * ) Notice: Subject to any disclaimer, the term of this patent is extended or adjusted under 35 U.S.C. 154(b) by 480 days.

(21) Appl. No.: 17/606,329

(22) PCT Filed: Apr. 23, 2020

(86) PCT No.: PCT/IB2020/053872
§ 371 (c)(1),
(2) Date: Sep. 22, 2022

(87) PCT Pub. No.: WO2020/217215
PCT Pub. Date: Oct. 29, 2020

(65) Prior Publication Data
US 2023/0000237 A1    Jan. 5, 2023

(30) Foreign Application Priority Data
Apr. 24, 2019   (CO) .............................. 2019/0004080

(51) Int. Cl.
*A45F 3/04*  (2006.01)
*A45F 3/00*  (2006.01)

(52) U.S. Cl.
CPC ........ *A45F 3/047* (2013.01); *A45F 2003/003* (2013.01); *A45F 2003/045* (2013.01)

(58) Field of Classification Search
CPC .. A45F 3/04; A45F 3/042; A45F 3/047; A45F 3/06; A45F 2003/045; A61F 17/00
See application file for complete search history.

(56) References Cited

U.S. PATENT DOCUMENTS 4,212,392 A * 7/1980 McKenzie ............. A45C 13/02
                                                206/592
4,609,084 A * 9/1986 Thomas ................. A61F 17/00
                                                190/110

(Continued)

FOREIGN PATENT DOCUMENTS

CN     202425843 U    9/2012
CN     203138877 U    8/2013

(Continued)

*Primary Examiner* — Justin M Larson
(74) *Attorney, Agent, or Firm* — Patenting Consulting Group; Roberto J. Rios

(57) ABSTRACT

The present patent application relates to a backpack for domiciliary medical services, for optimising the transport, protection, cleaning and organisation of basic medical items (devices and consumables) when used in the care of a patient during his or her respective domiciliary medical visit and consultation by a doctor or health professional. The backpack for domiciliary medical services also allows easy access to the medical and personal items being carried, and provides versatile adjustment and adaptation of each of its interior spaces according to the need of the health professional. Furthermore, using oxygen, UV light, water, soap or ammonia, among others, the backpack and all the items that it contains can be cleaned and disinfected against microor- (Continued)

ganisms and bacteria that may become impregnated in or adhere to the backpack.

10 Claims, 28 Drawing Sheets

(56) References Cited

U.S. PATENT DOCUMENTS

| | | | | |
|---|---|---|---|---|
| 4,844,307 A * | 7/1989 | Rutledge | .................... | A45F 3/04 |
| | | | | 224/636 |
| 8,534,523 B2 * | 9/2013 | Murdoch | .................. | A45F 3/04 |
| | | | | 224/648 |
| 2008/0314947 A1 * | 12/2008 | Gold | .......................... | A45F 3/04 |
| | | | | 224/628 |
| 2009/0184143 A1 * | 7/2009 | Witt | .......................... | A45F 3/04 |
| | | | | 224/257 |
| 2010/0116860 A1 | 5/2010 | Tello | | |
| 2012/0217279 A1 | 8/2012 | Murdoch et al. | | |
| 2012/0325880 A1 * | 12/2012 | Yu | .......................... | A45C 15/06 |
| | | | | 224/576 |
| 2020/0352801 A1 * | 11/2020 | Bakkar | .................. | A45C 15/06 |
| 2024/0008626 A1 * | 1/2024 | Henderson | ............. | A45C 13/02 |

FOREIGN PATENT DOCUMENTS

| | | |
|---|---|---|
| CN | 109832772 A | 11/2017 |
| CN | 210248765 U | 4/2020 |
| EP | 3222167 A1 | 9/2017 |

\* cited by examiner

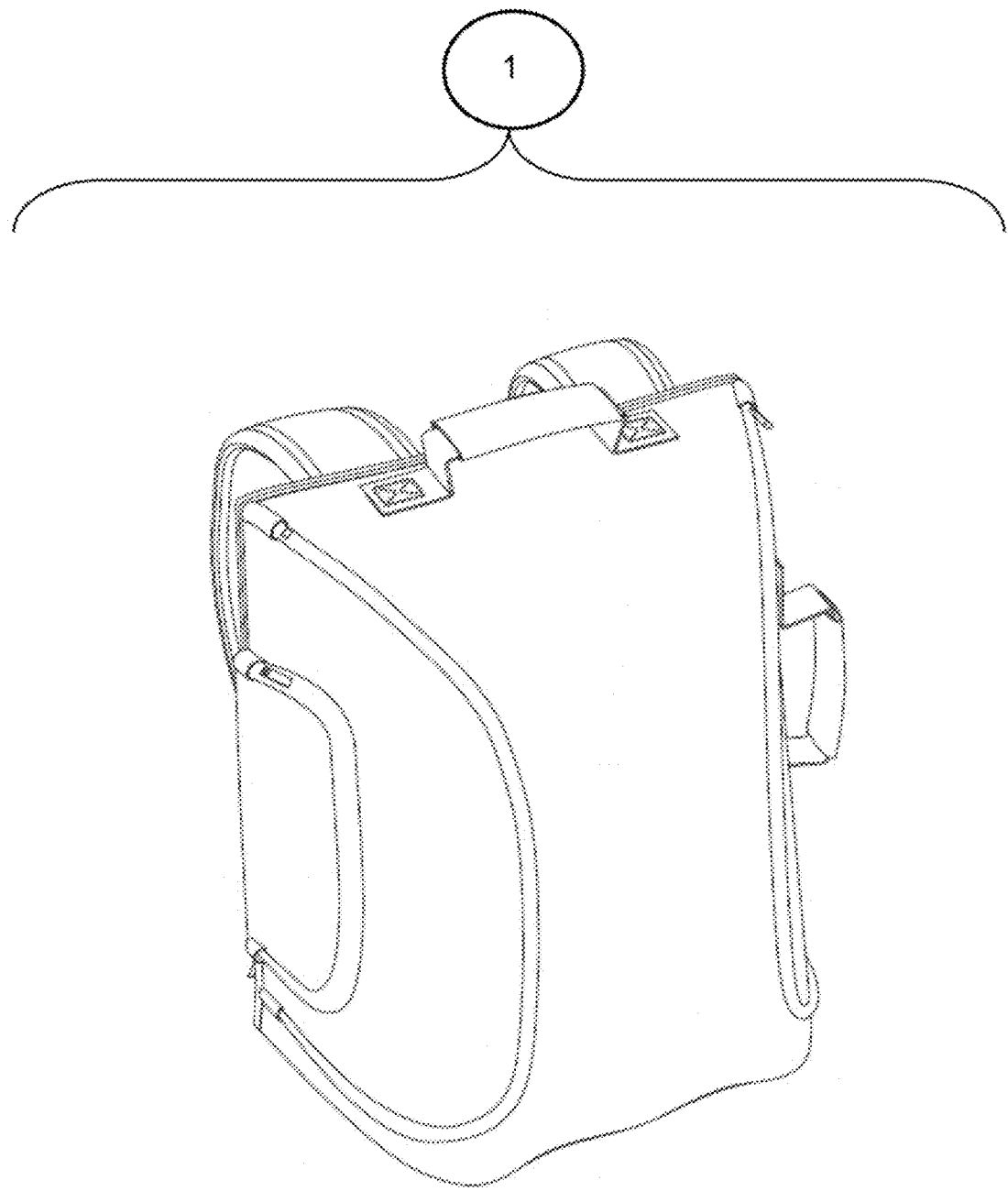
Fig. No 1

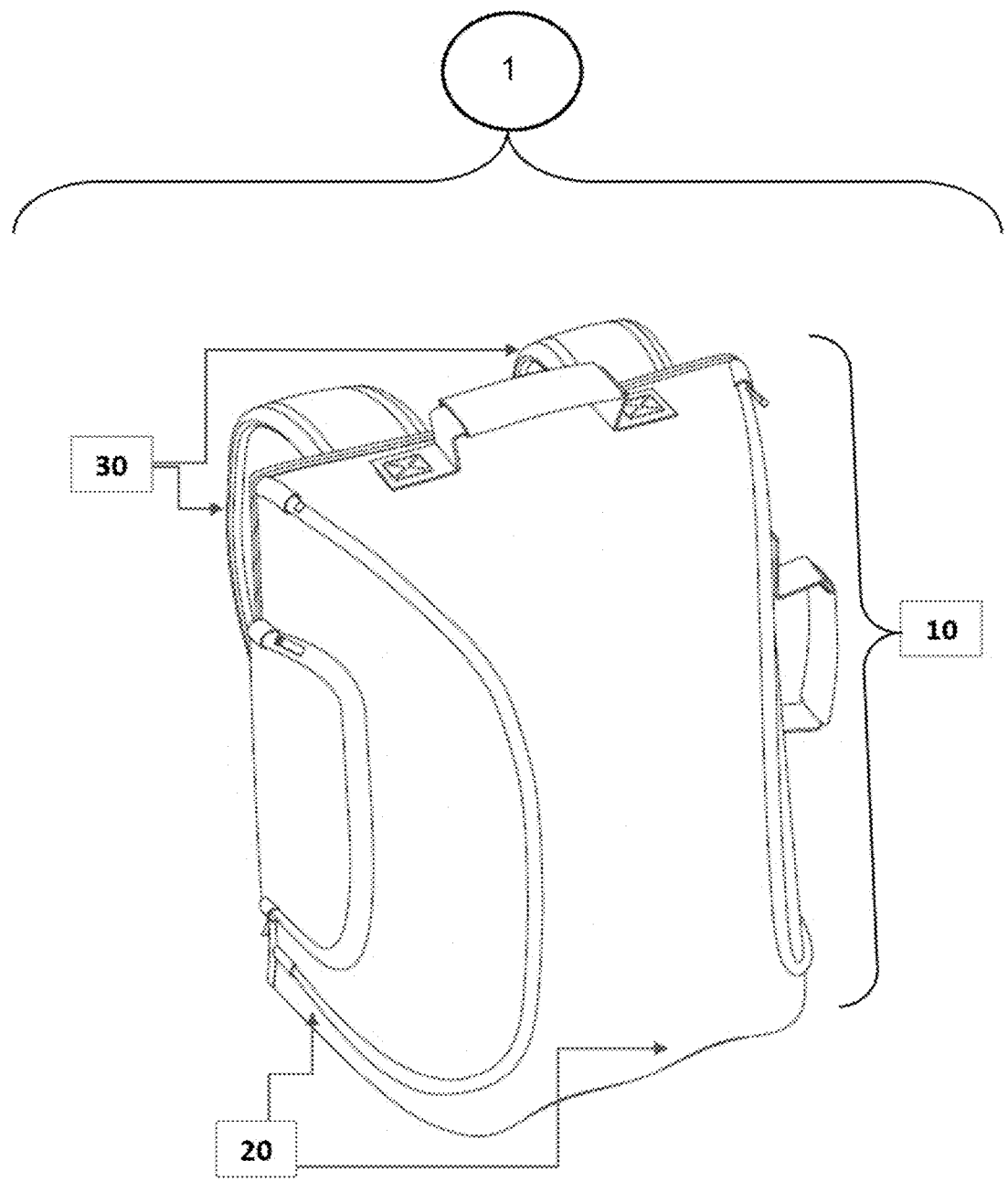
Fig. No 1A

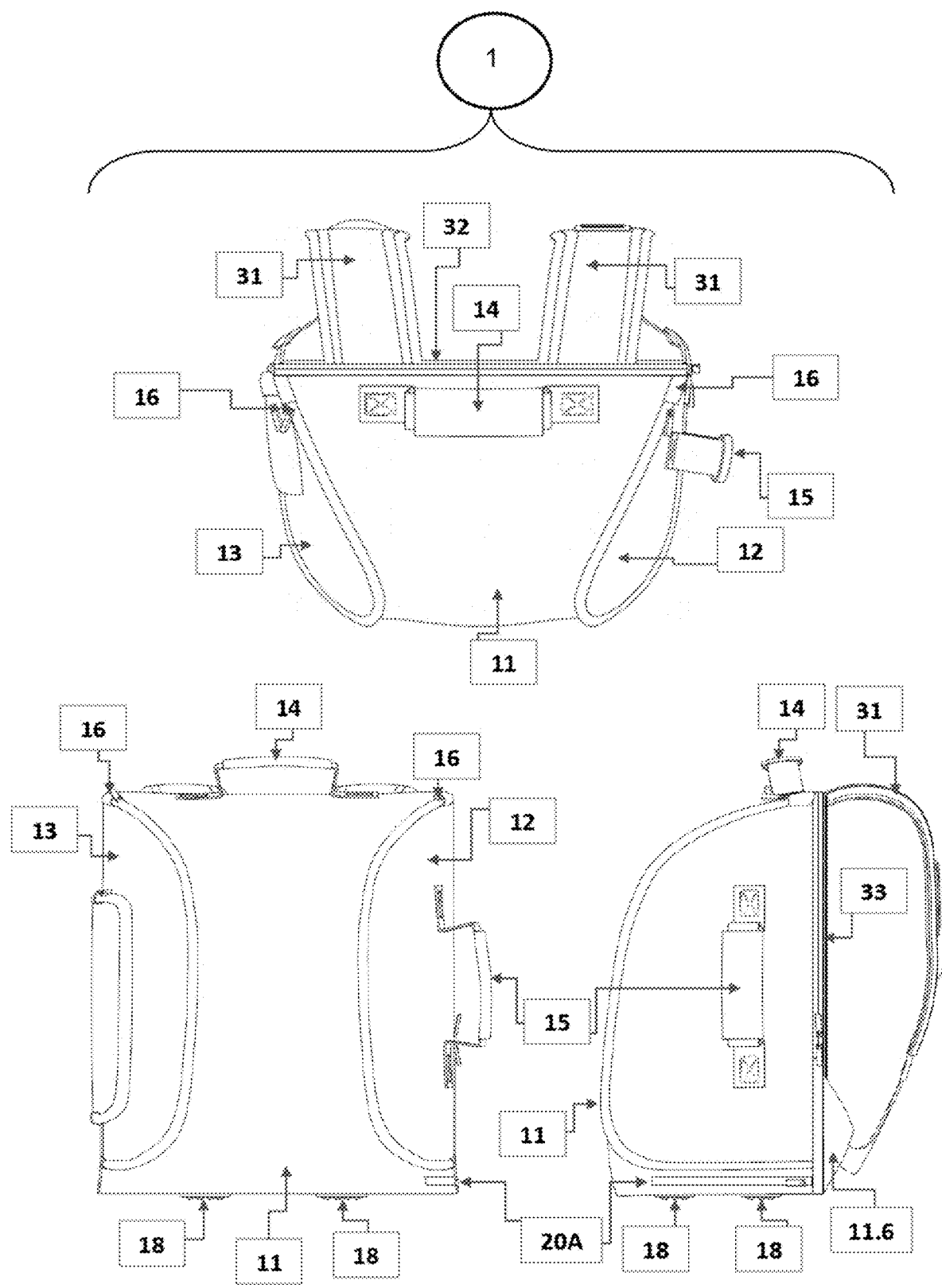
Fig. No 2

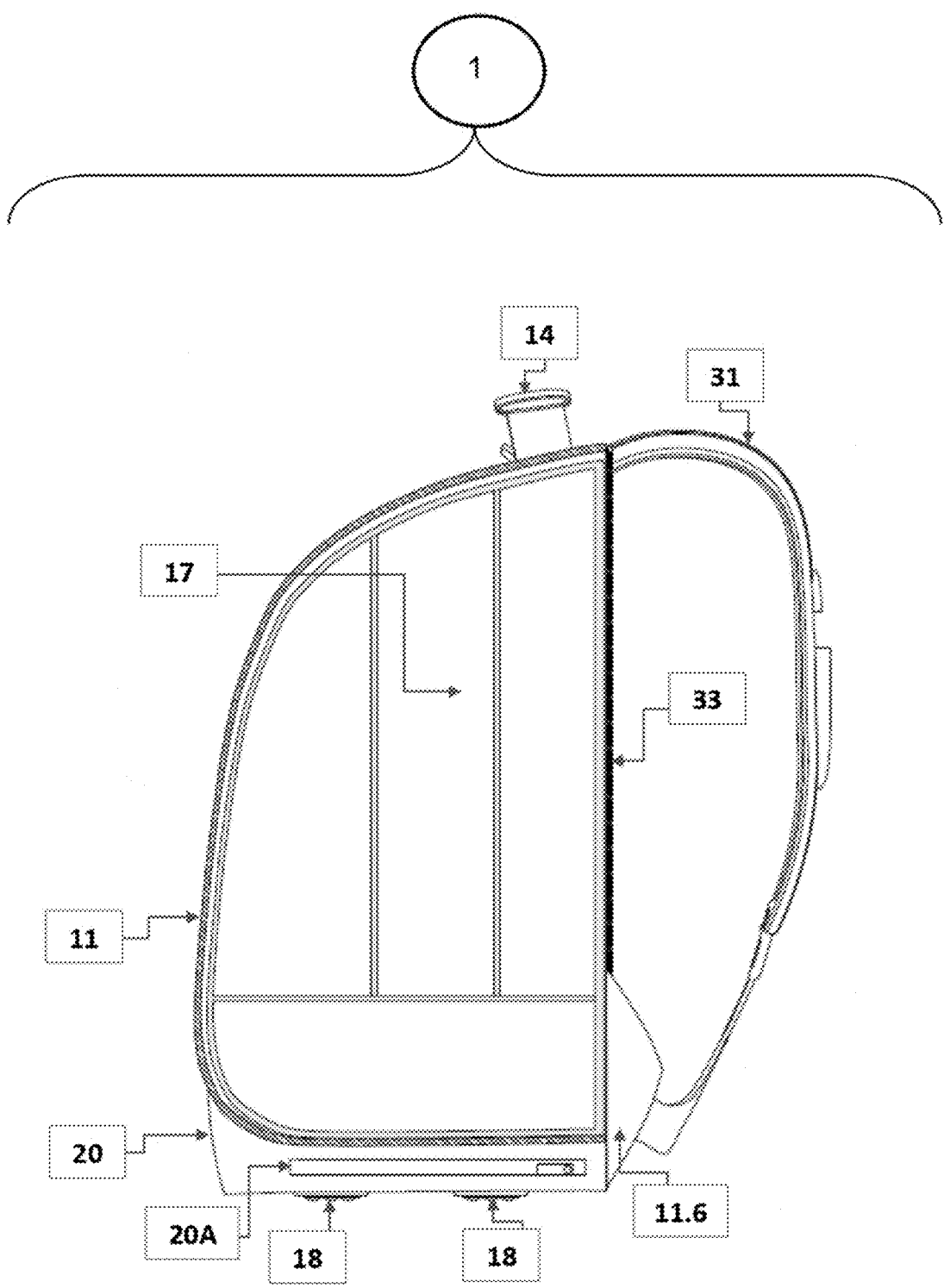
Fig. No 3

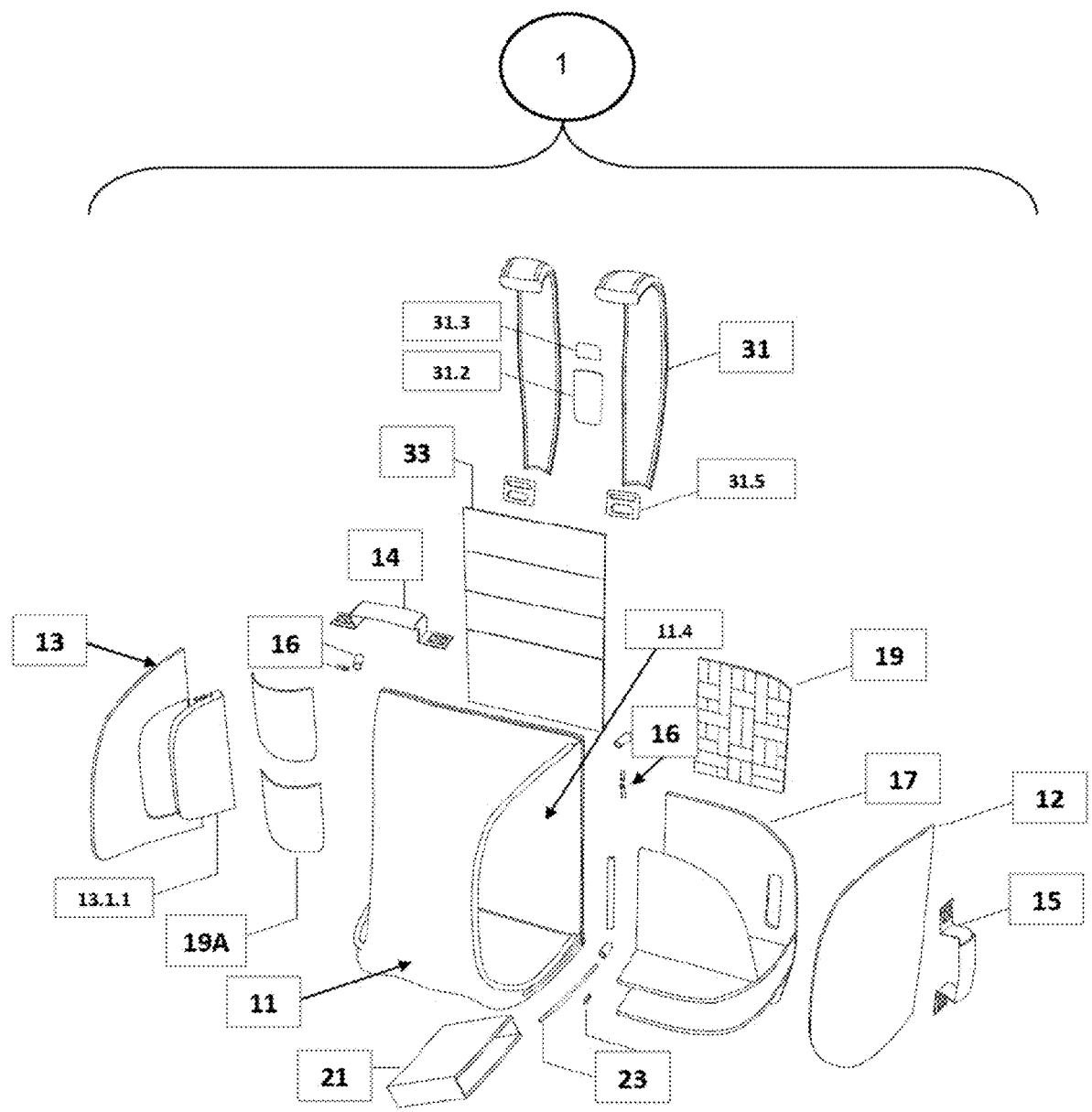
Fig. No 4

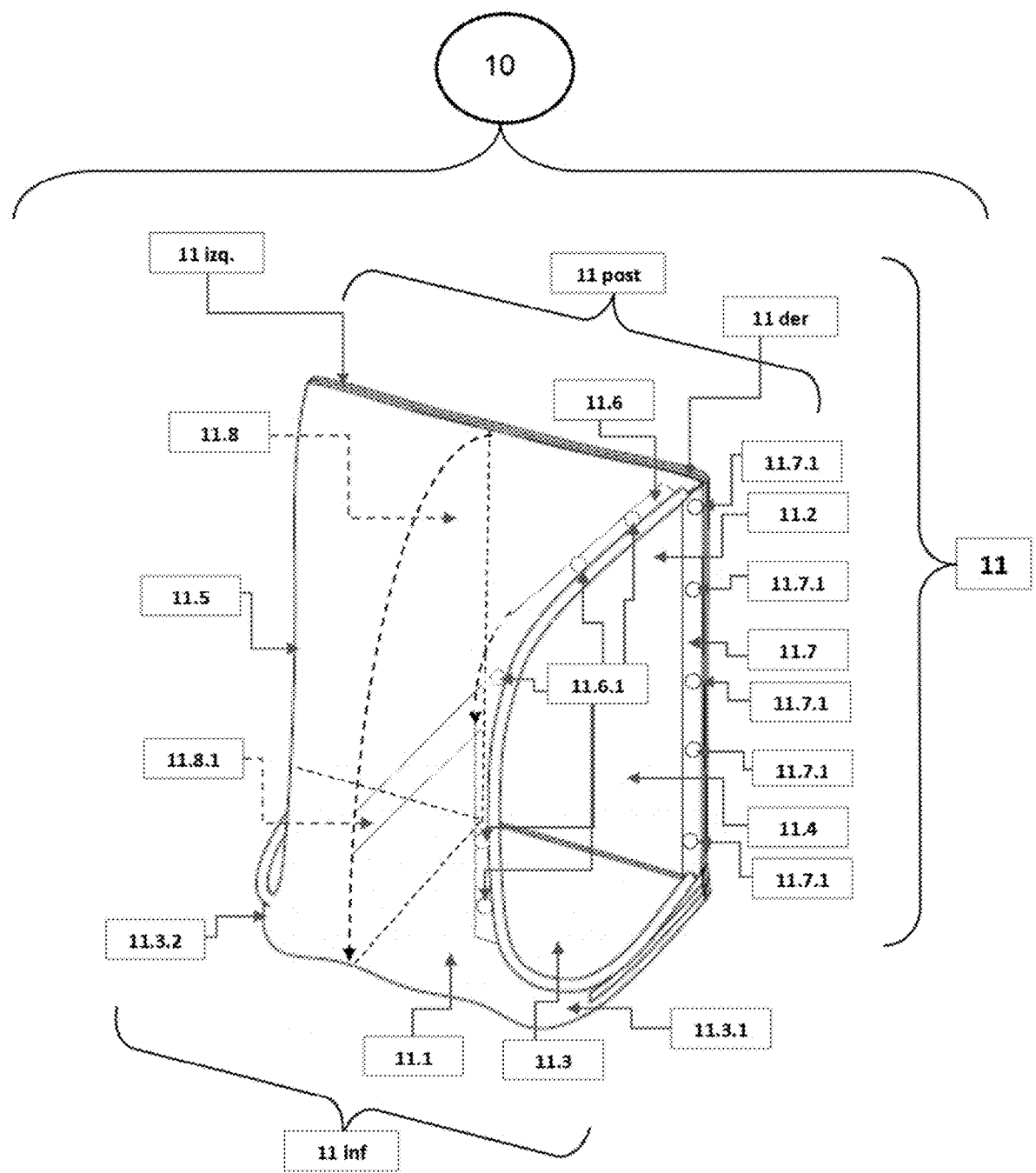
Fig. No 5

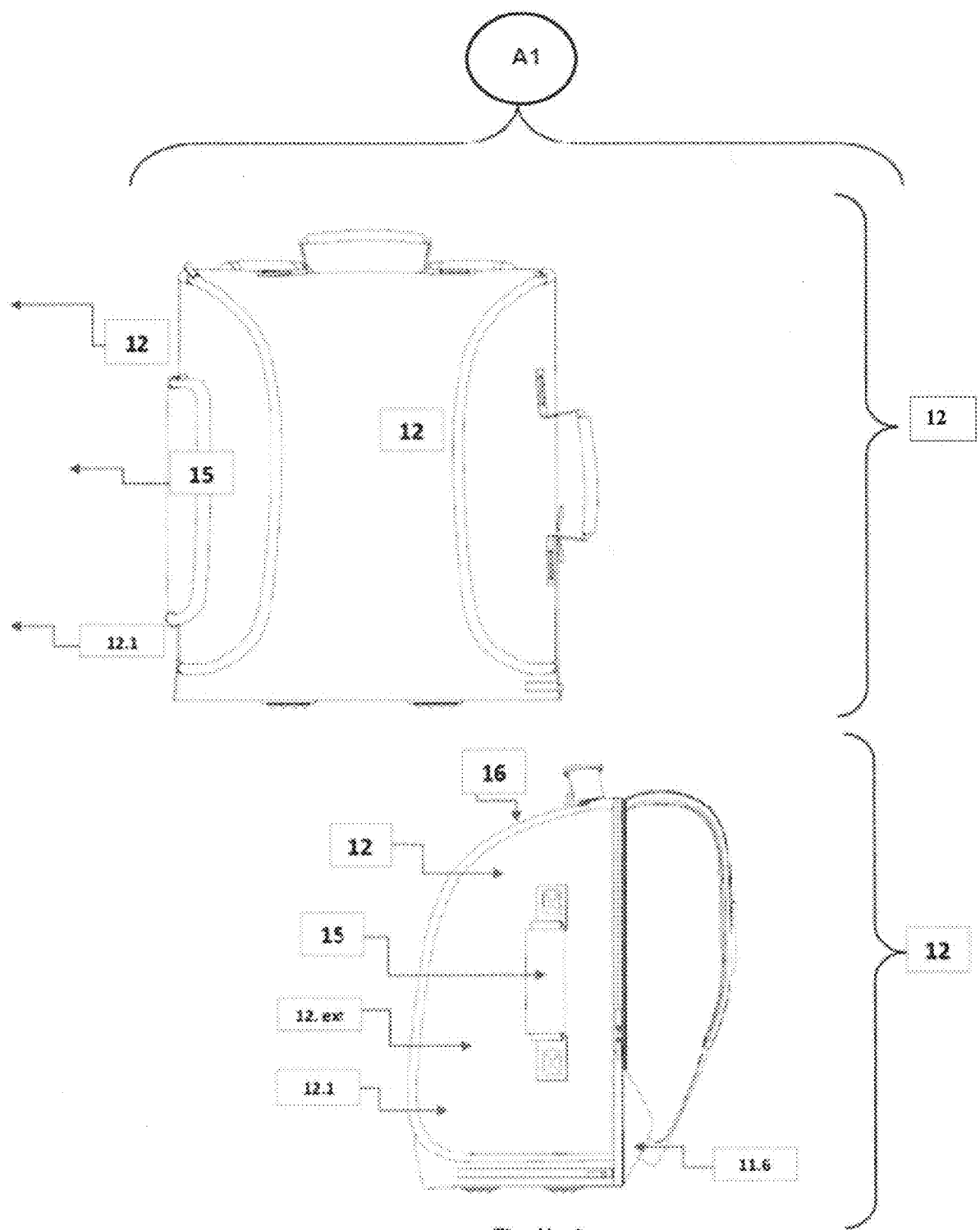
Fig. No 6

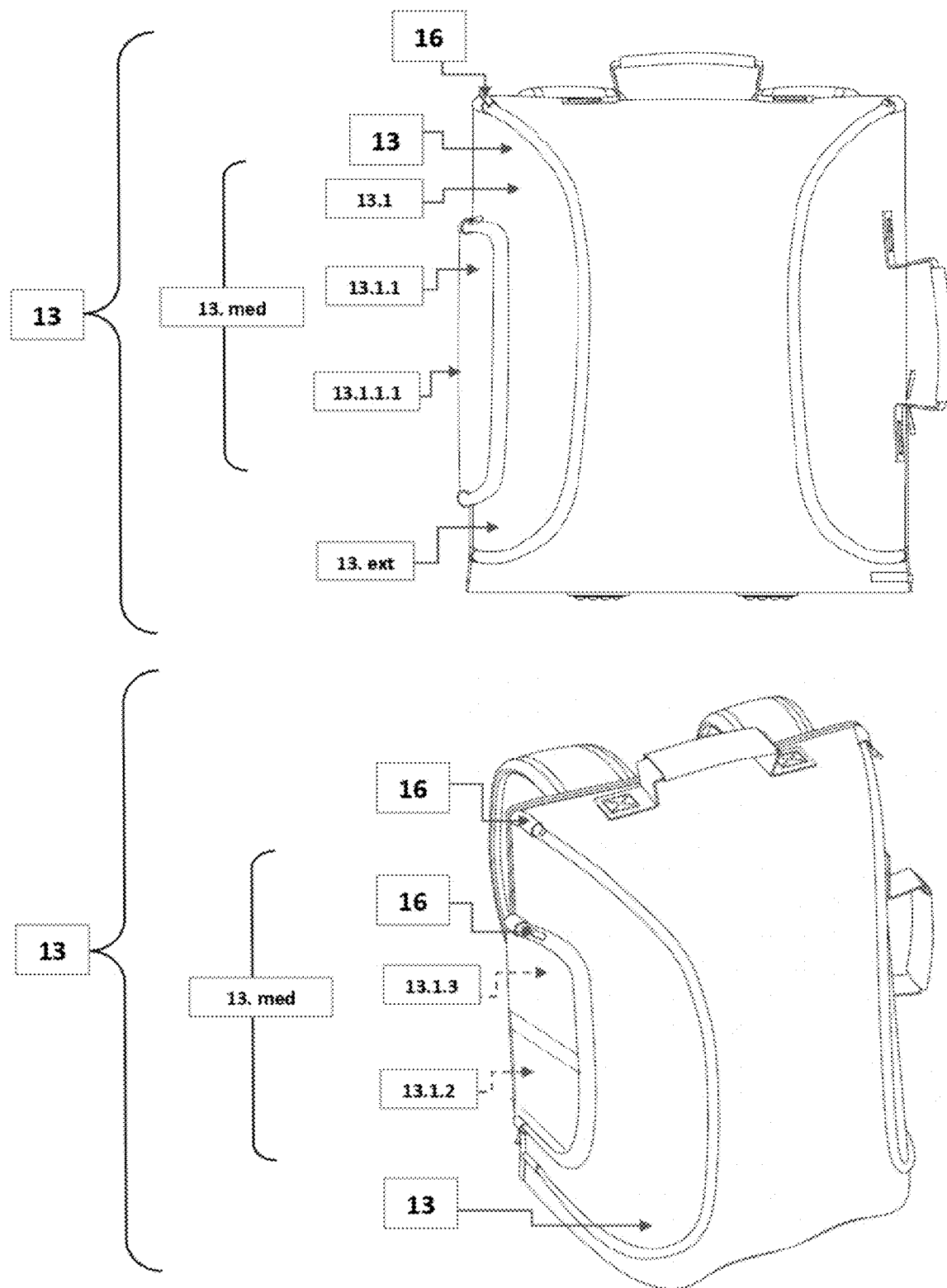
Fig. No 7

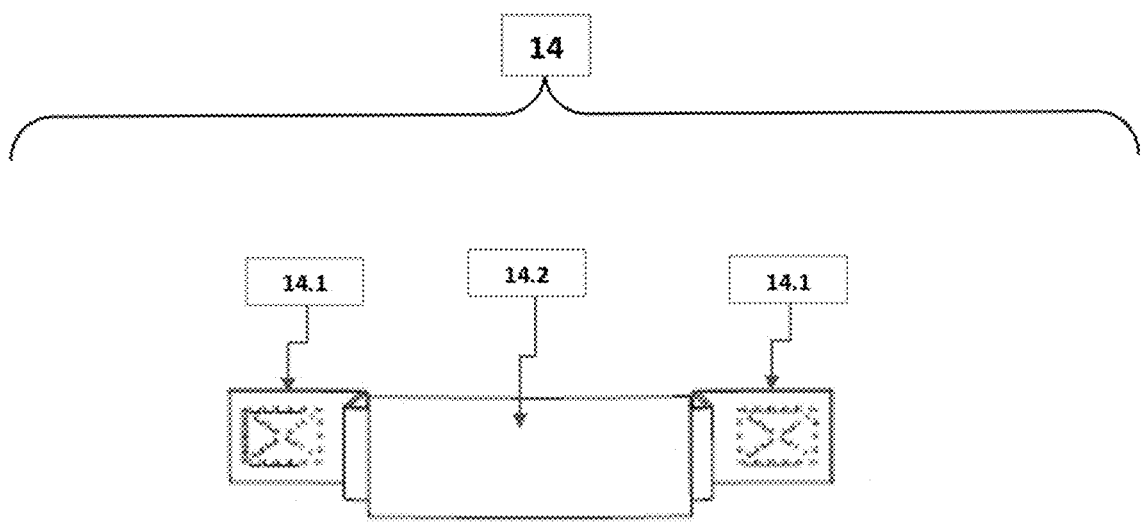
Fig. No 8
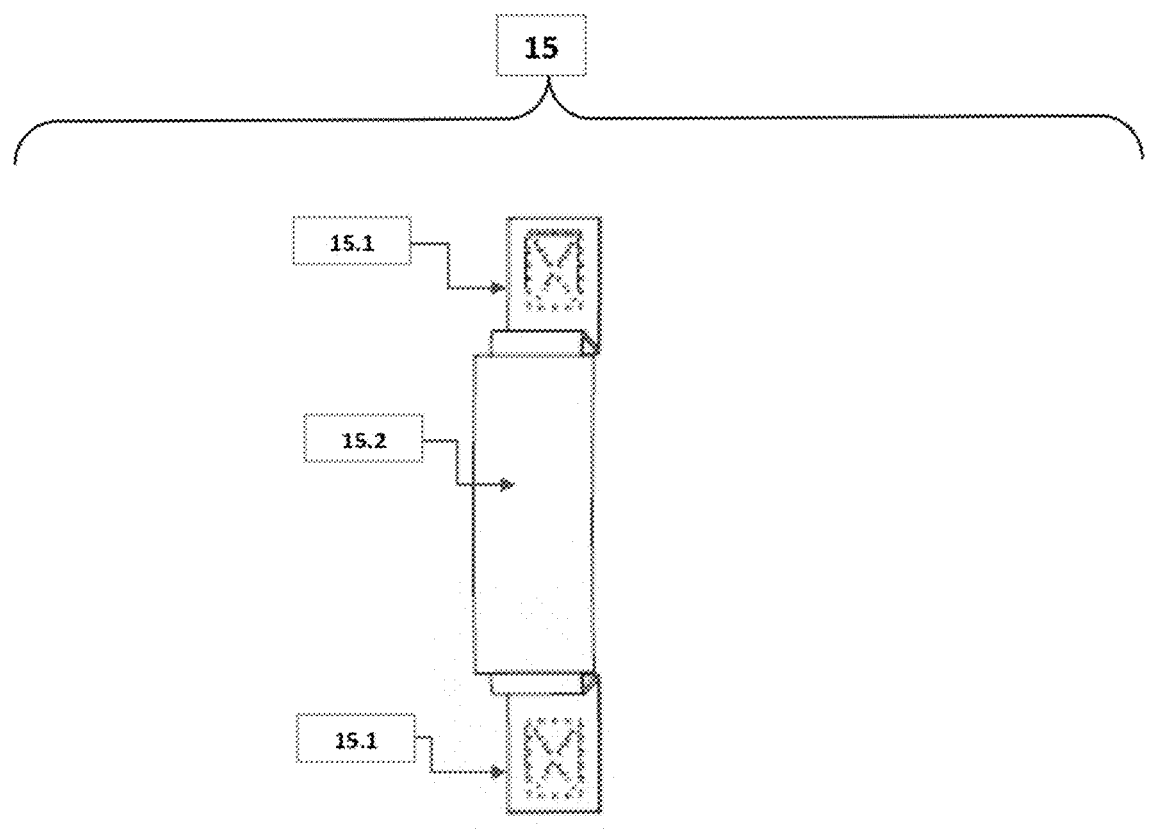
Fig. No 9

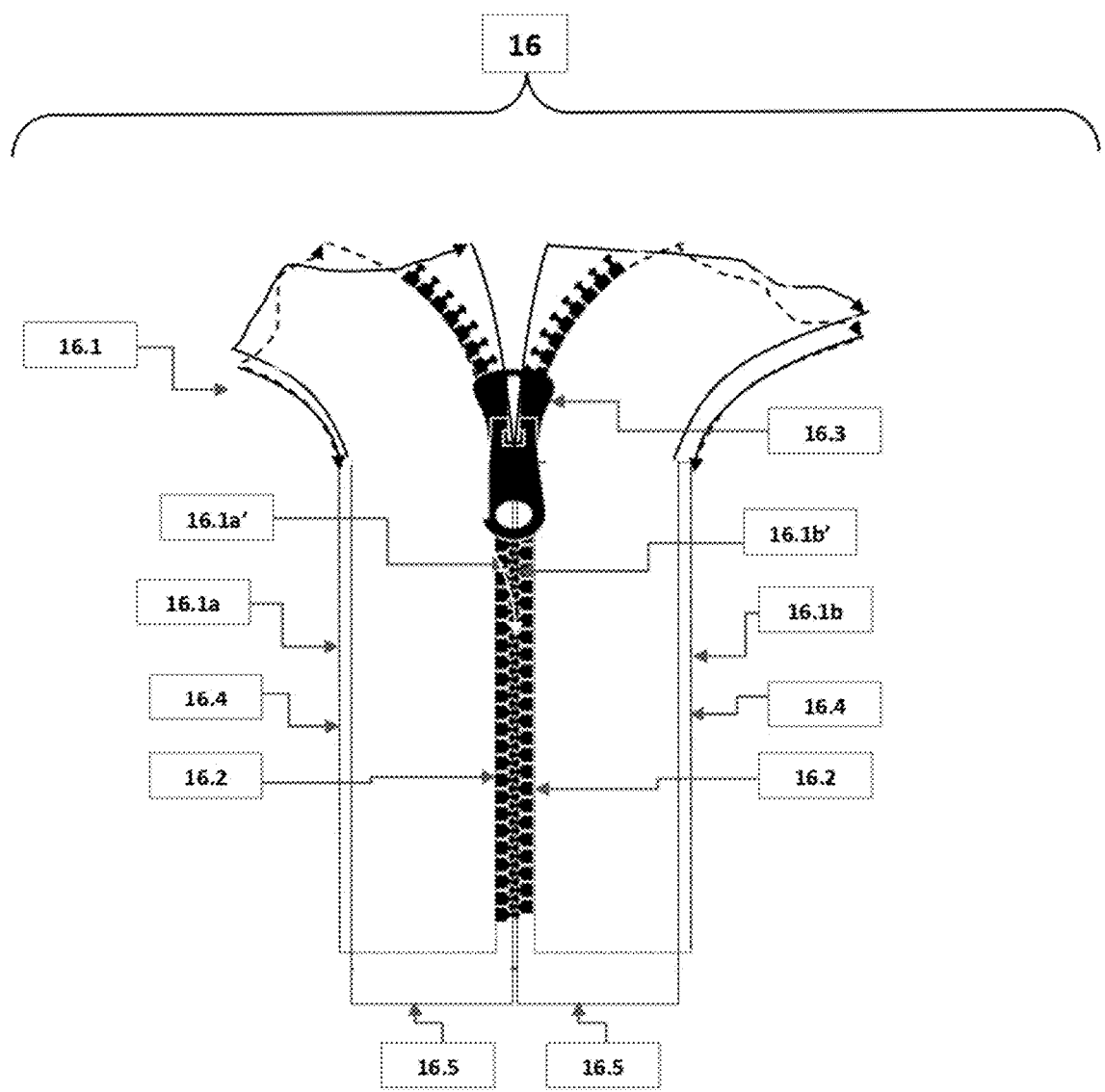
Fig. No 10

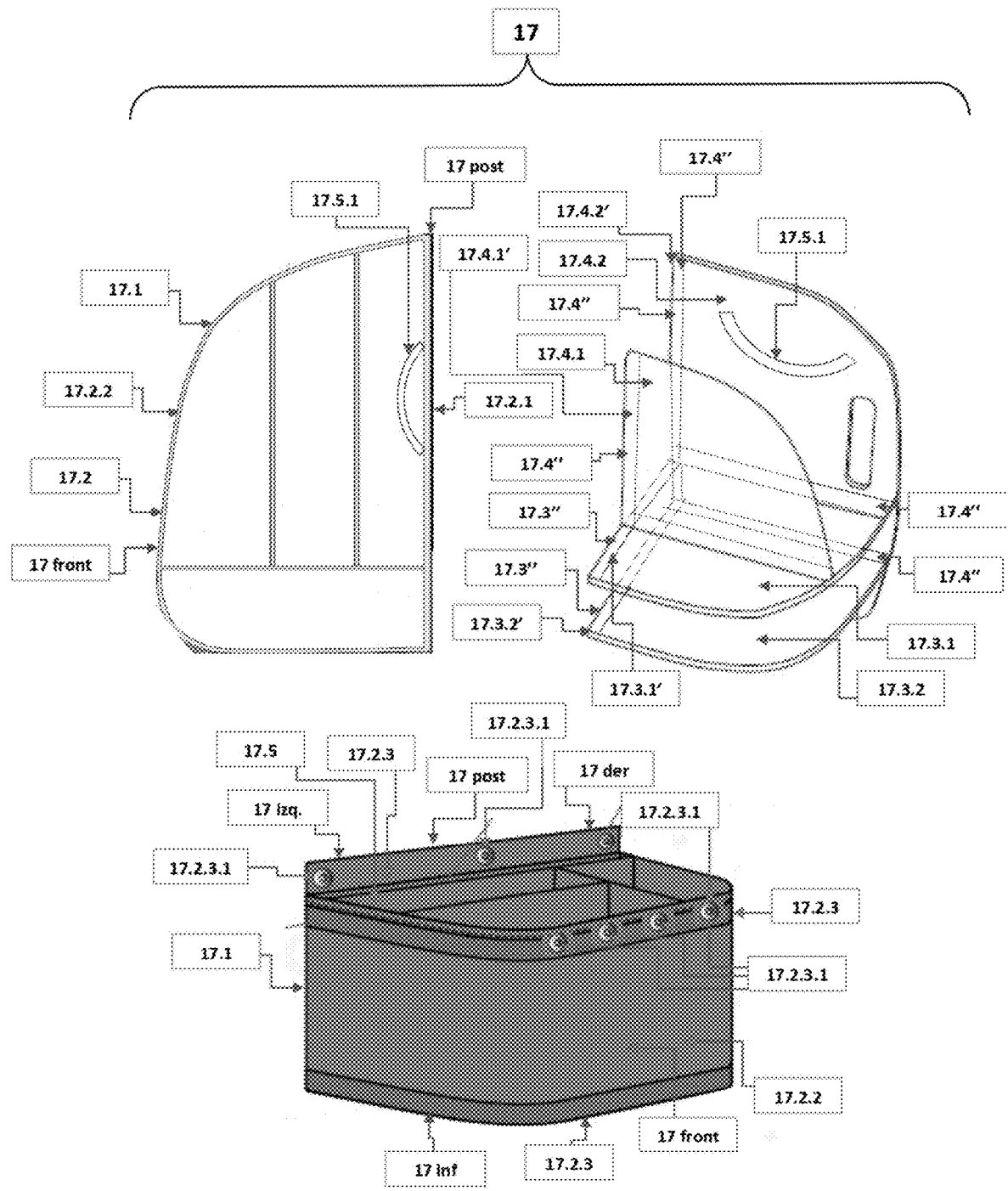
Fig. No 11

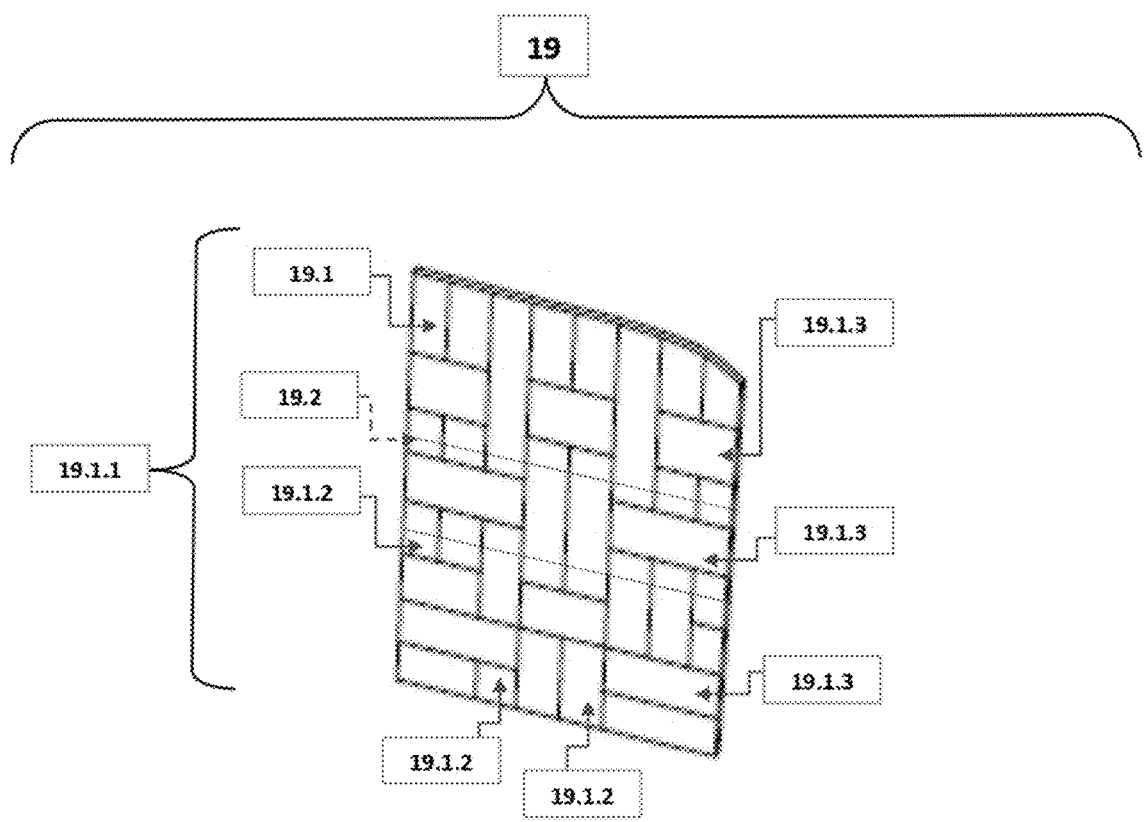
Fig. No 12
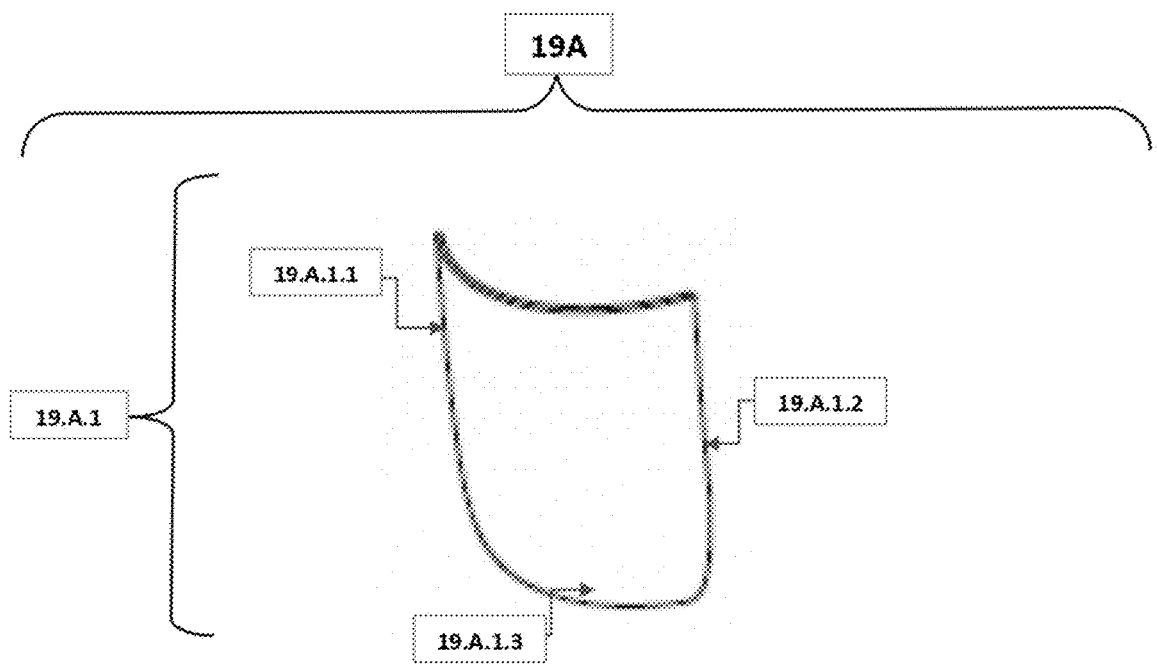
Fig. No 13

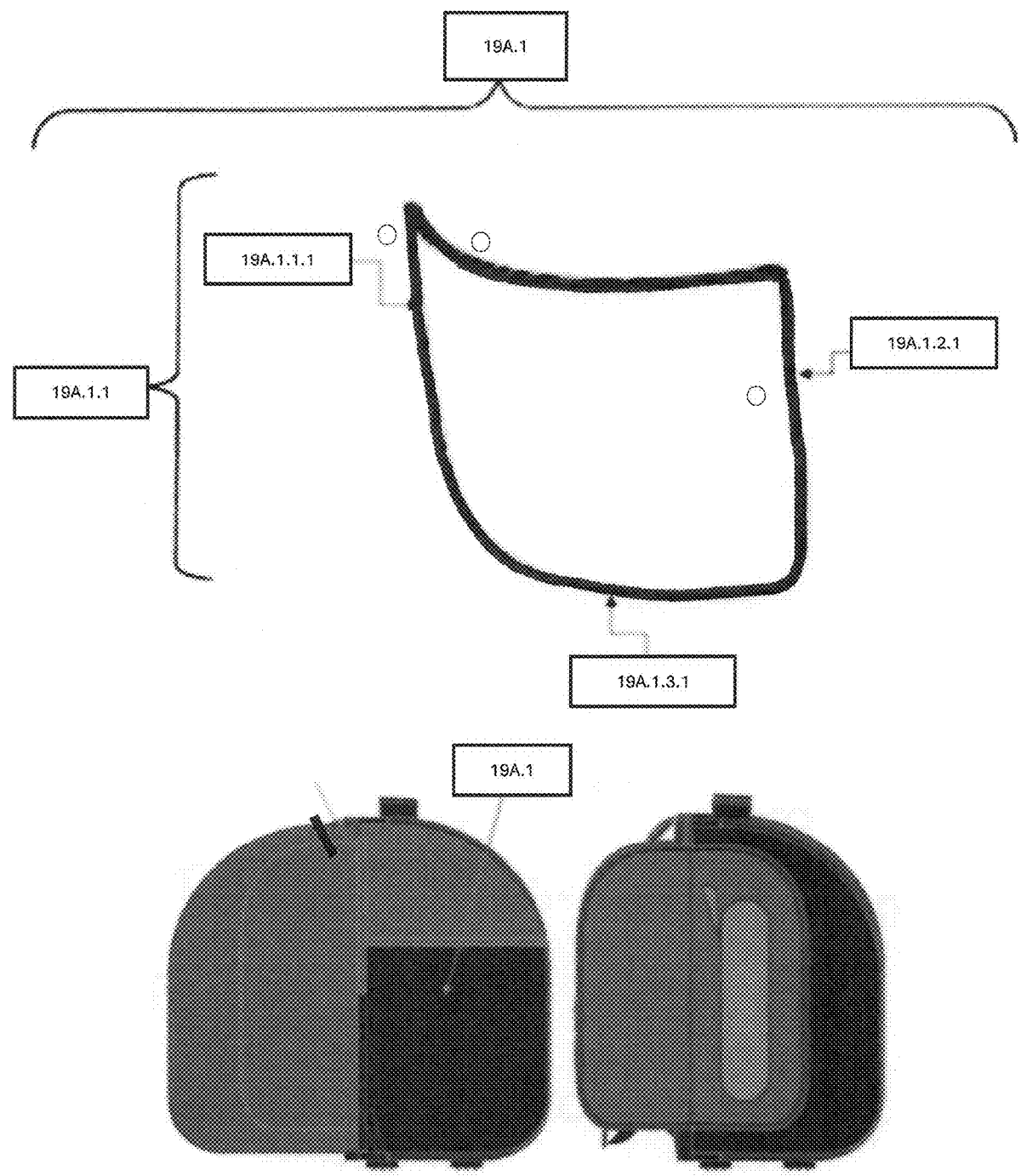
Fig. No. 14

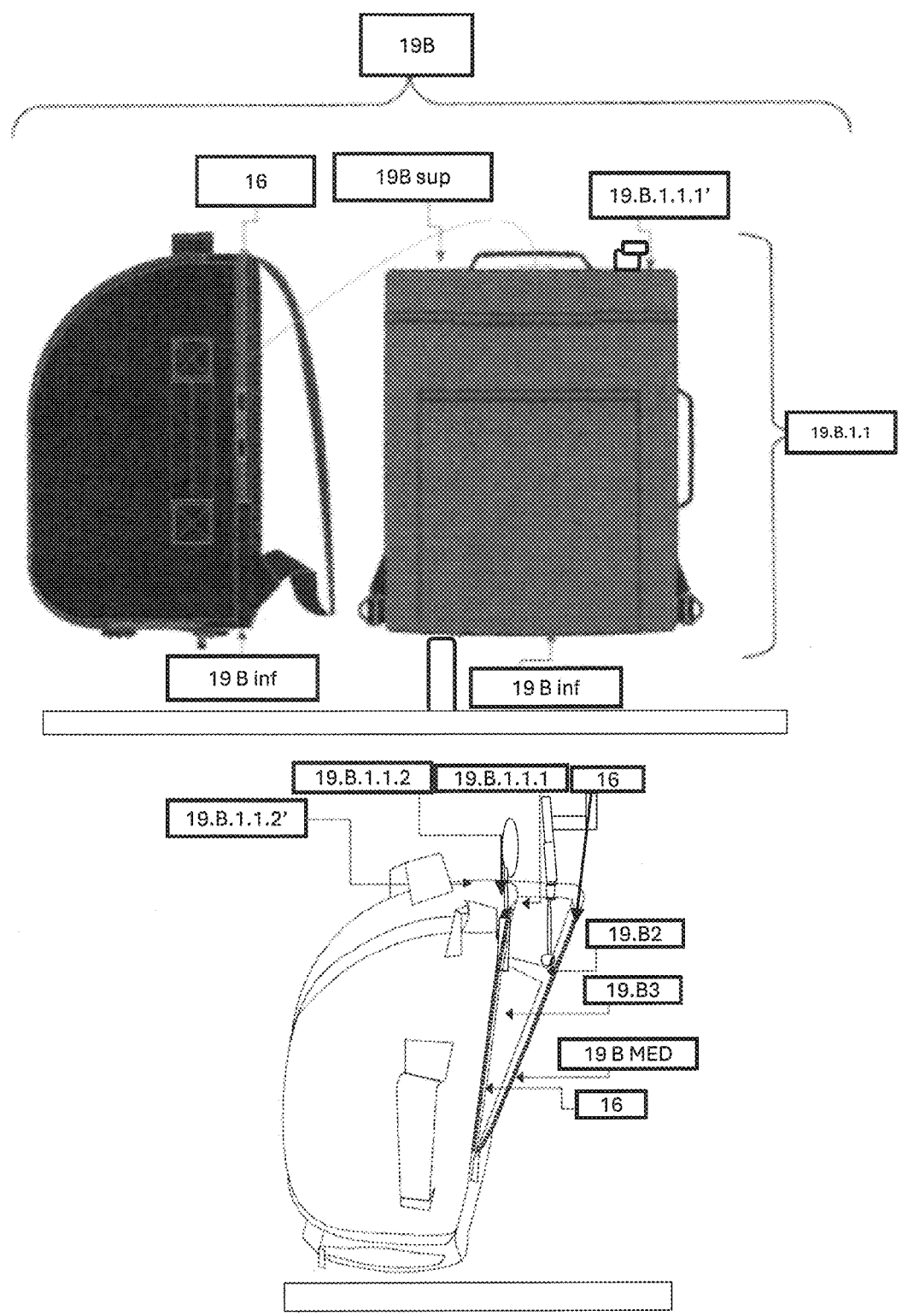
Fig. No. 15

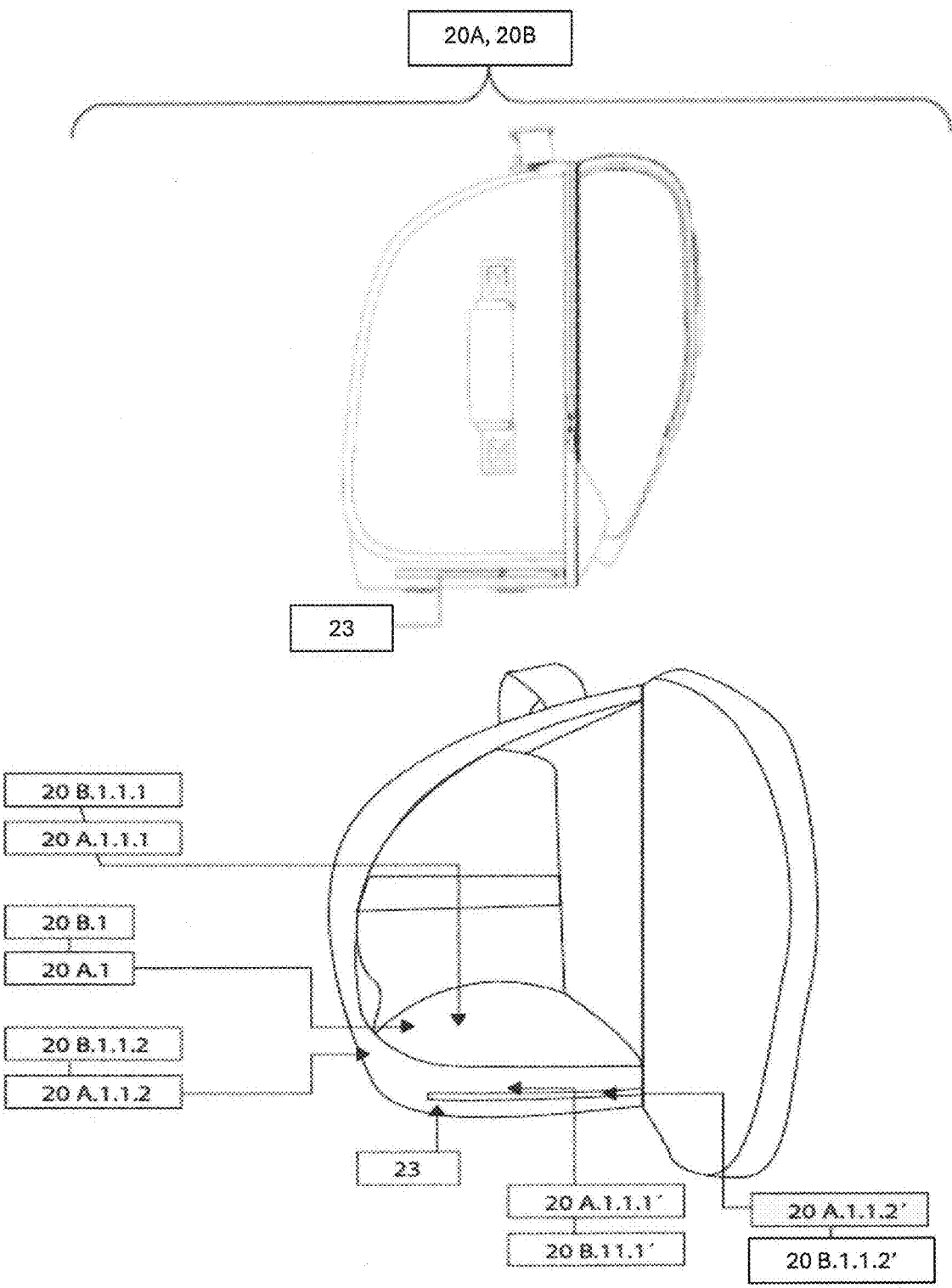
Fig. No. 16

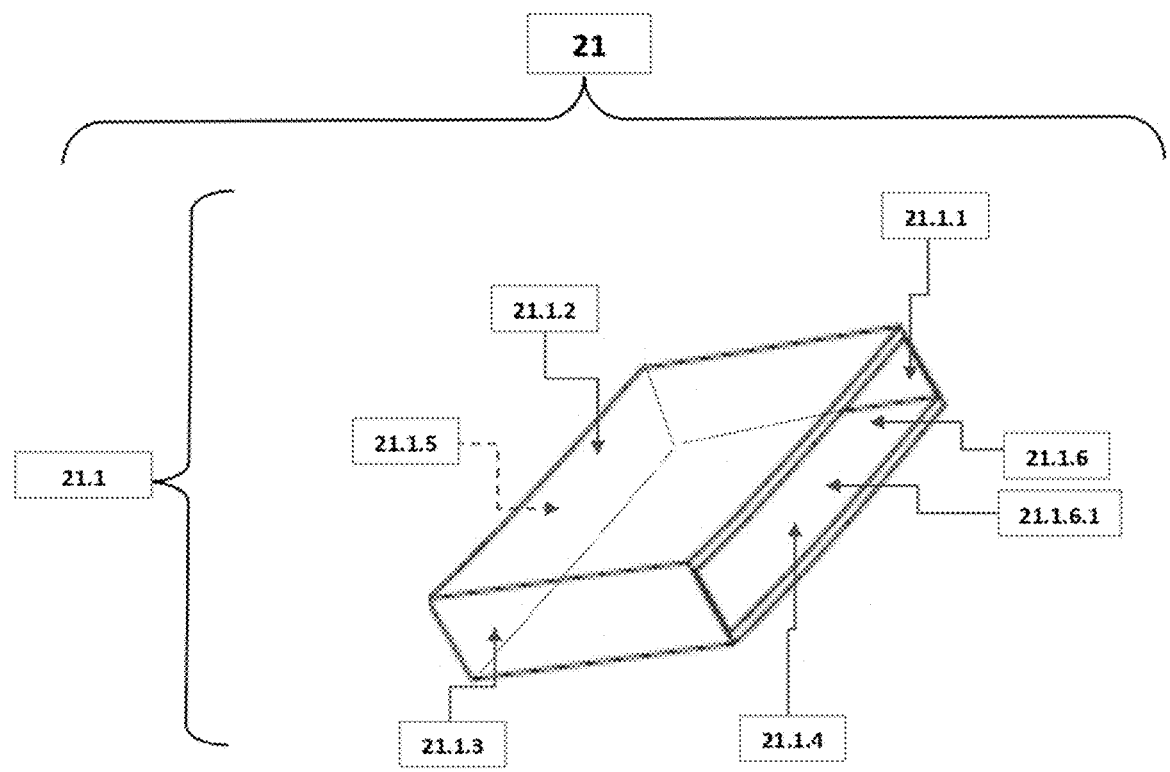
Fig. No 17
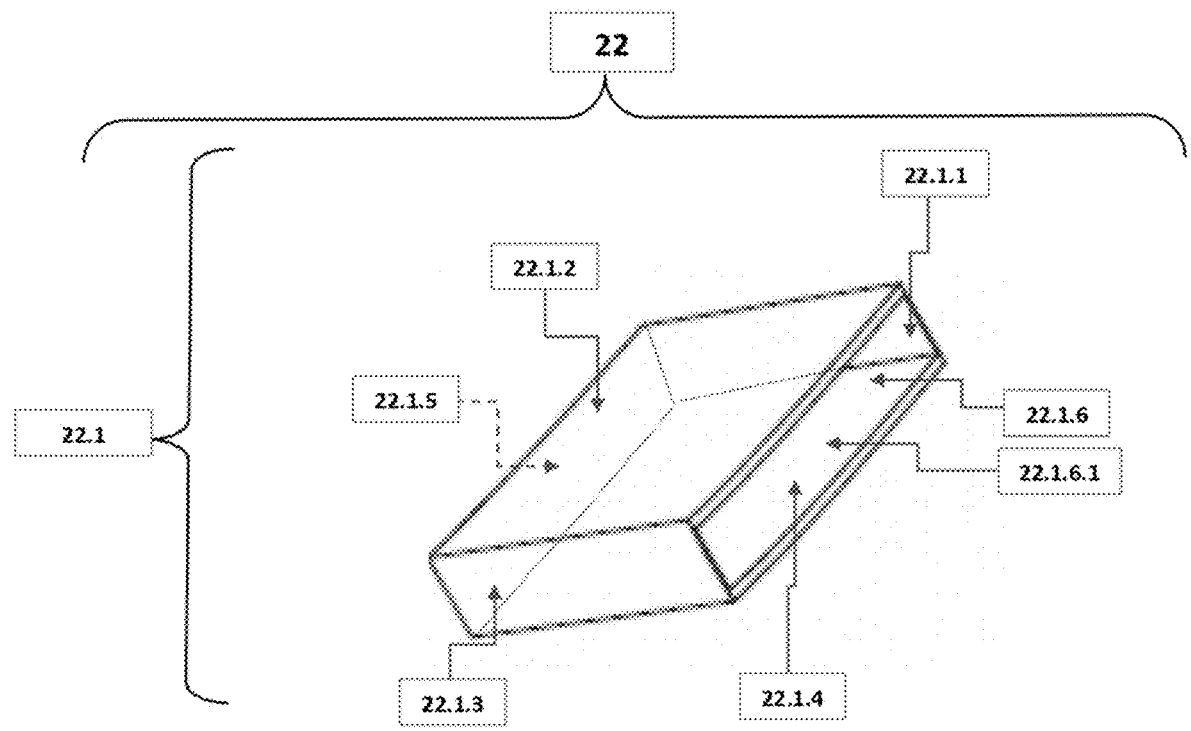
Fig. No 18

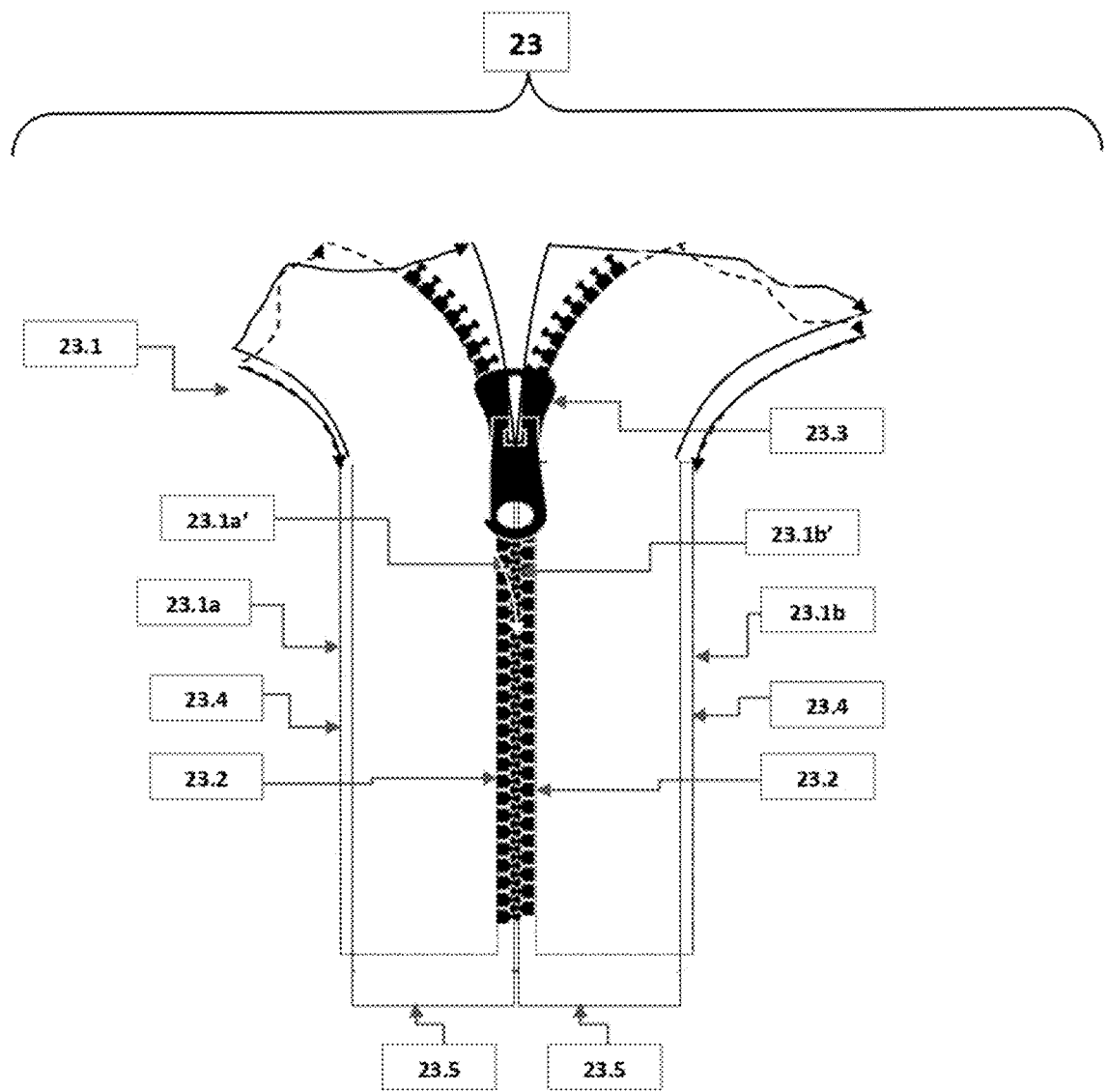
Fig. No 19

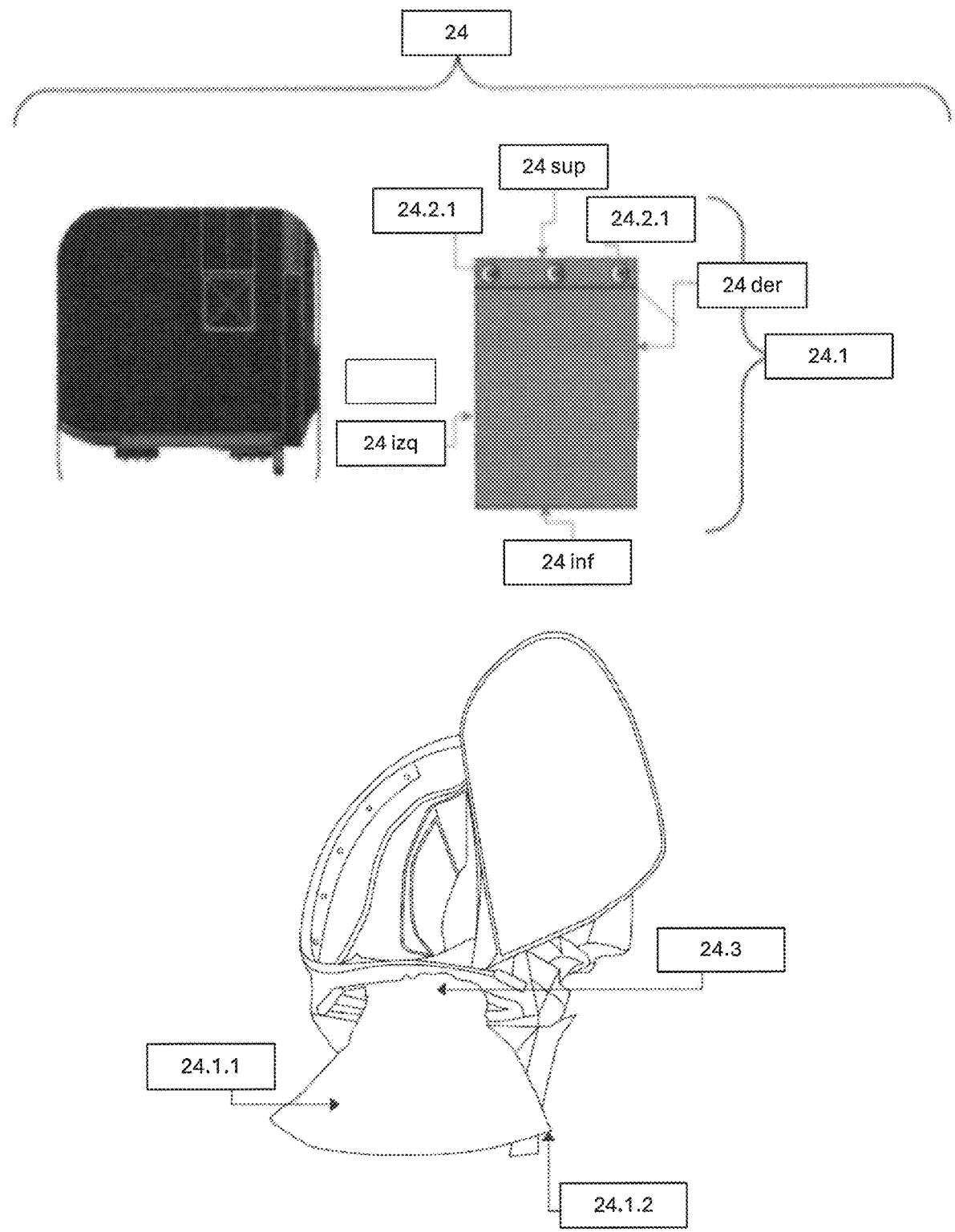
Fig. No. 20

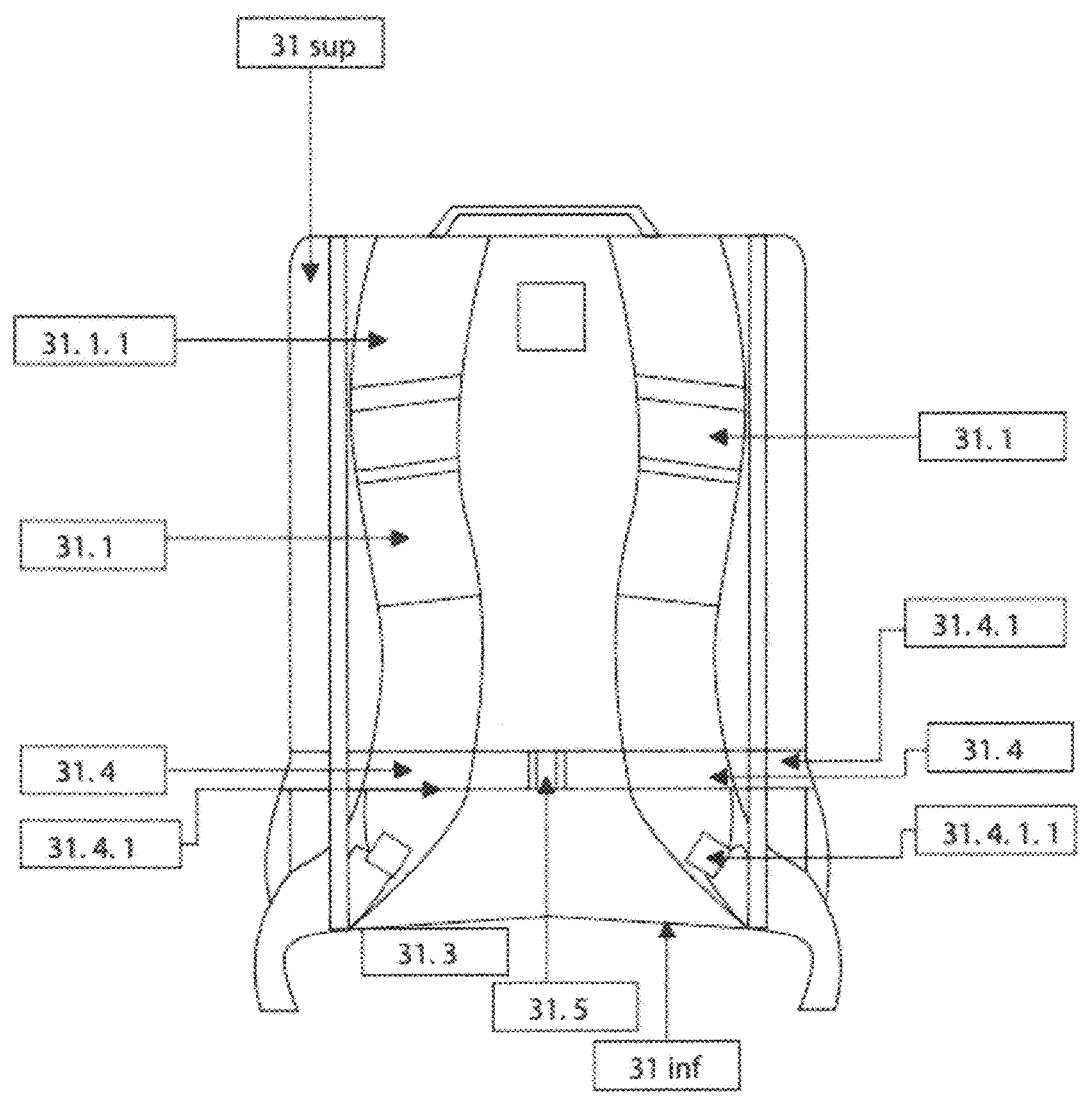
Fig. No. 21

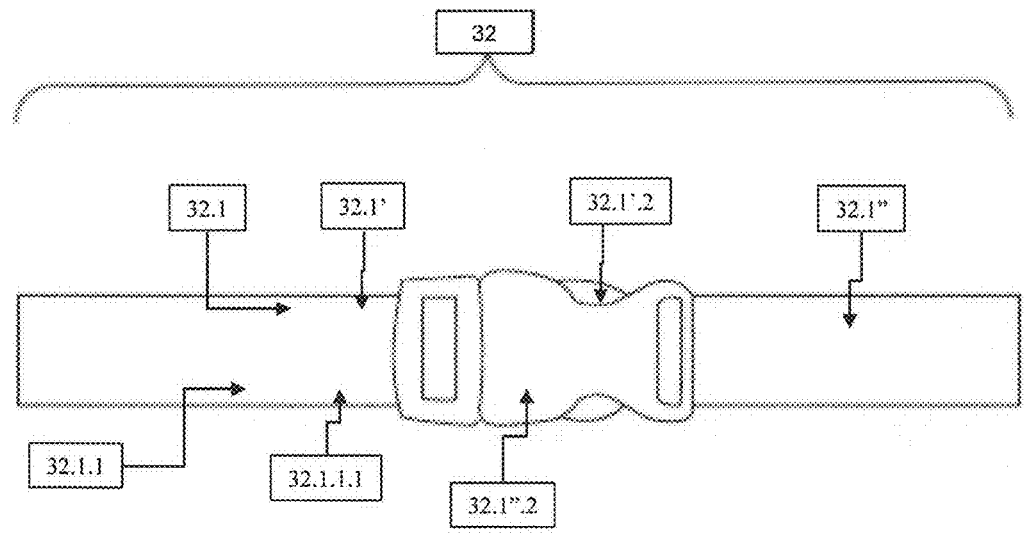
Fig. No. 22
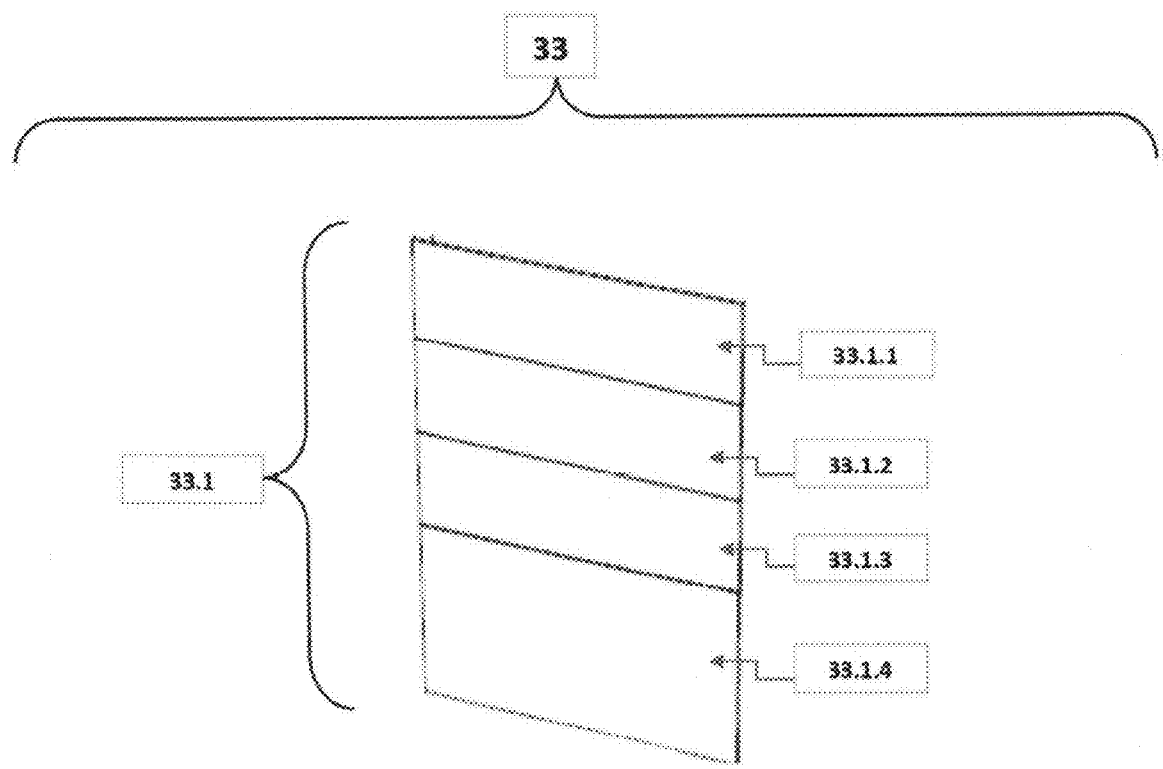
Fig. No. 23

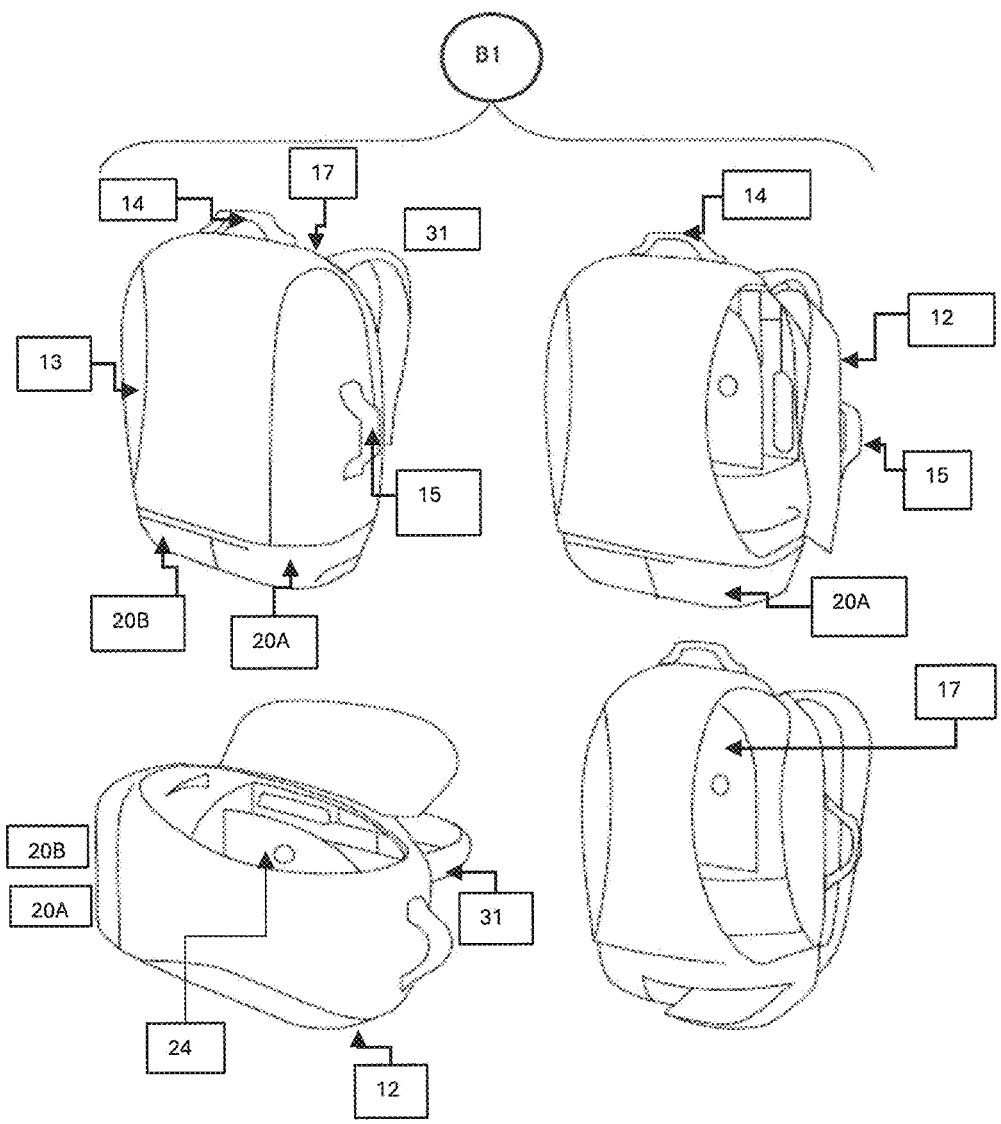
Fig. No. 24

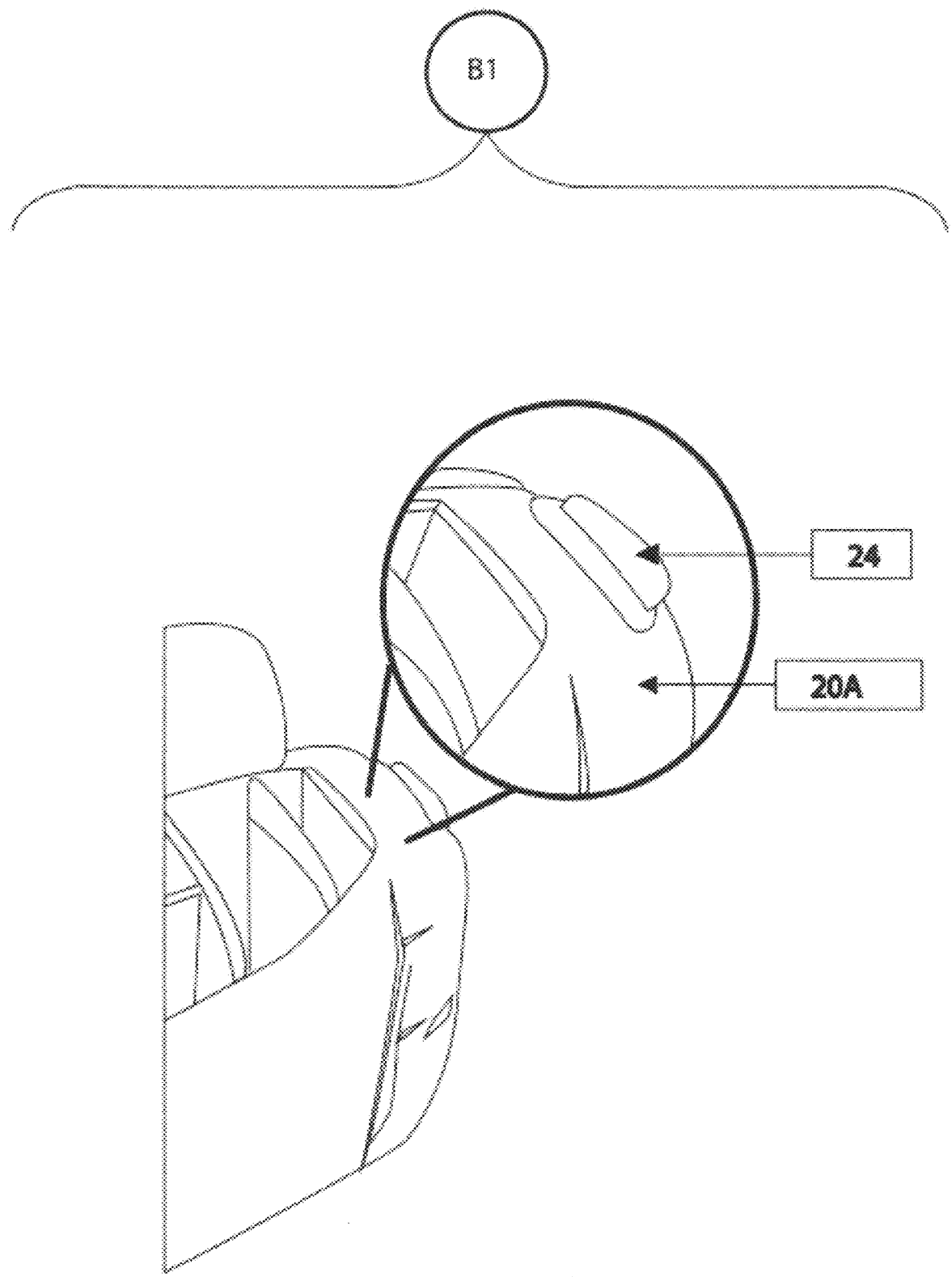
Fig. No. 25

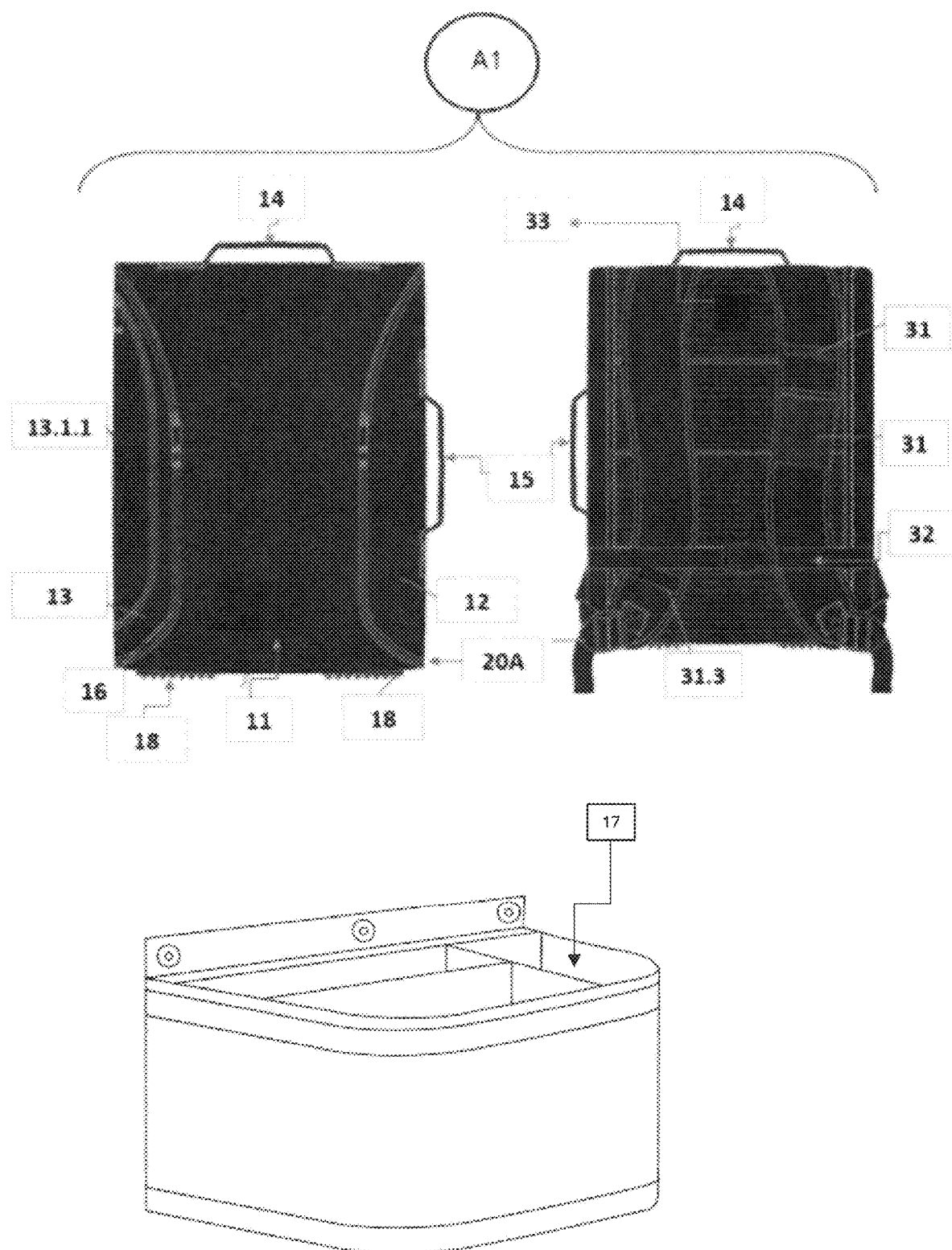
Fig. No. 26

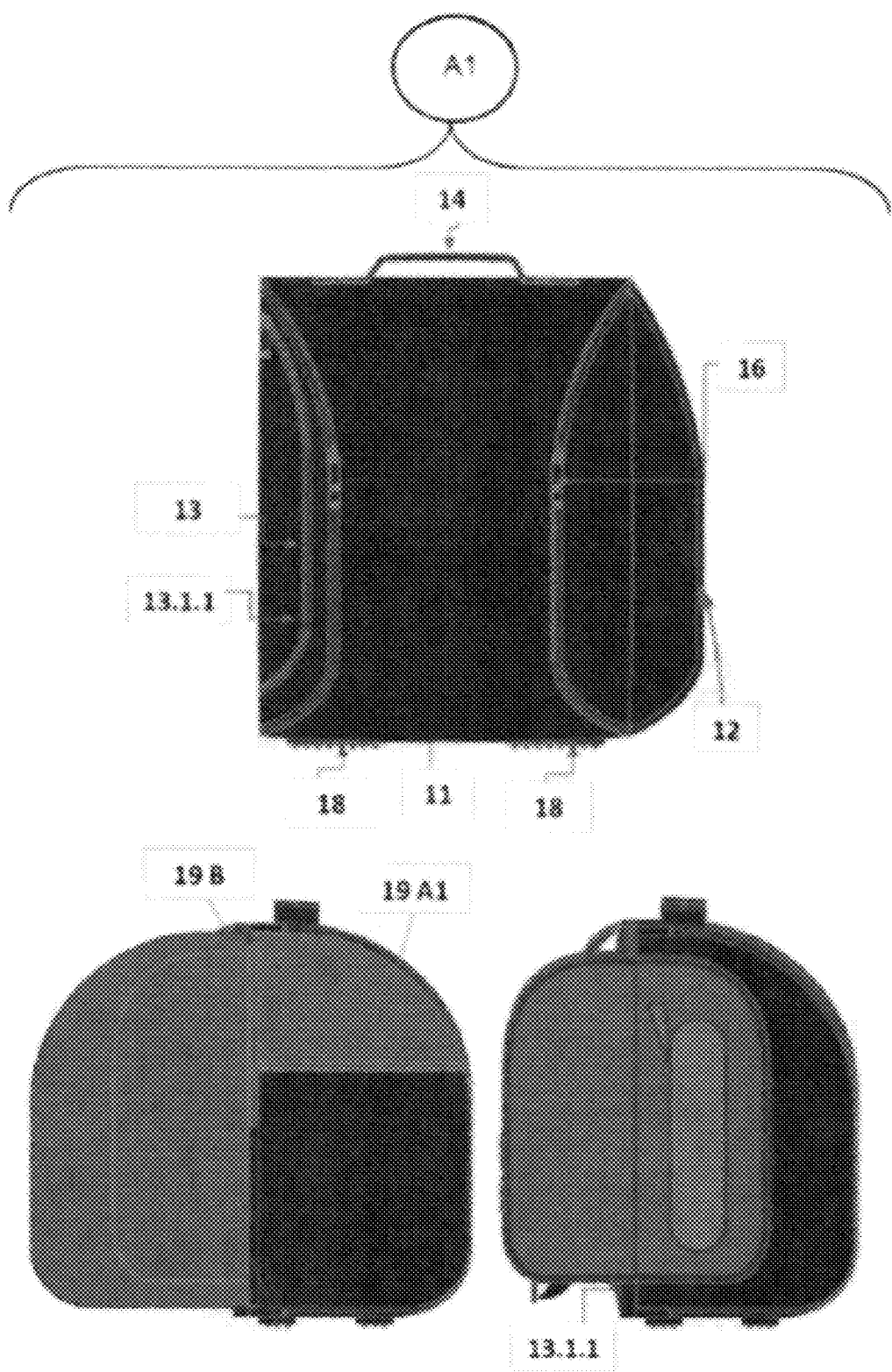
Fig. No. 27

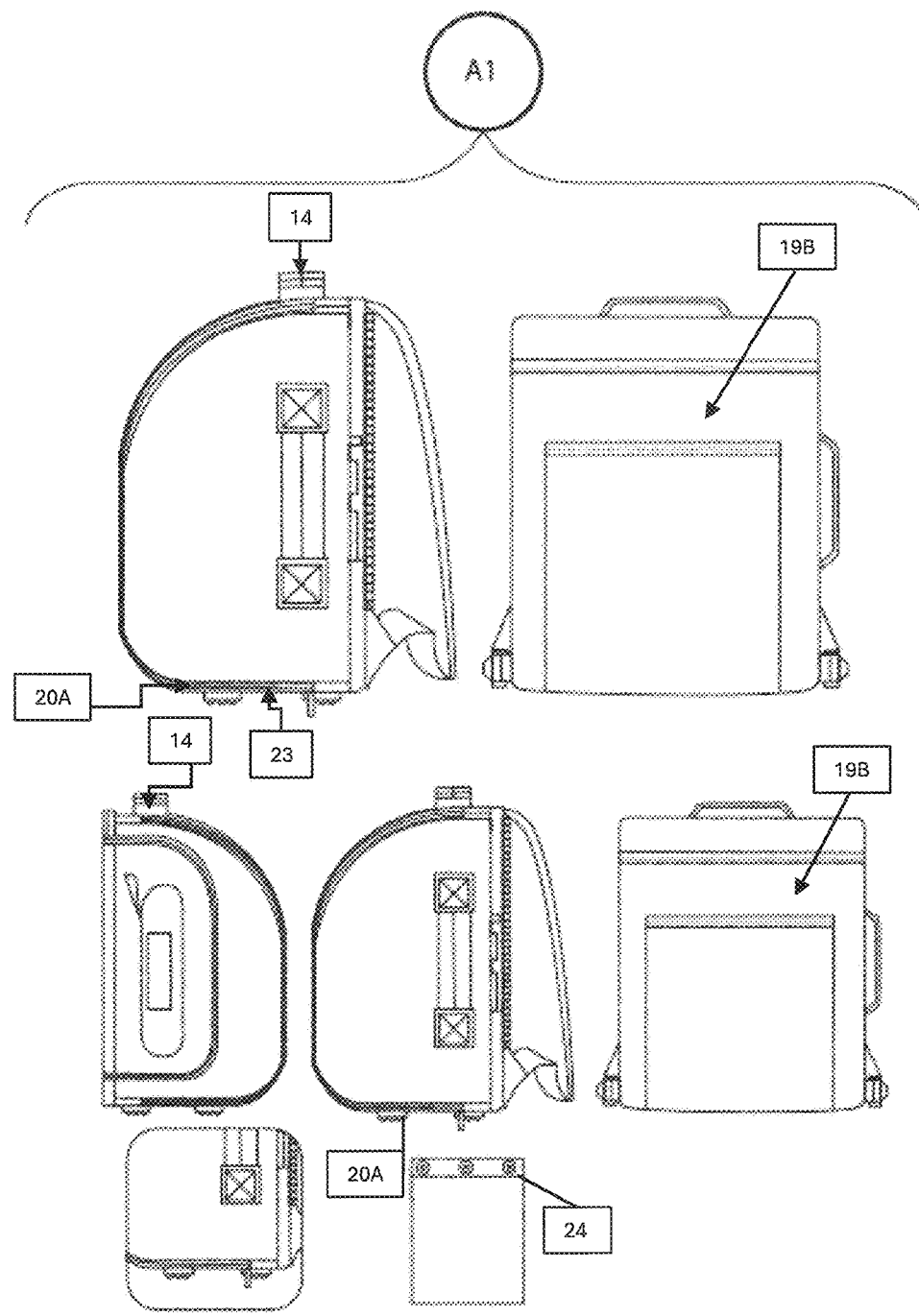
Fig. No. 28

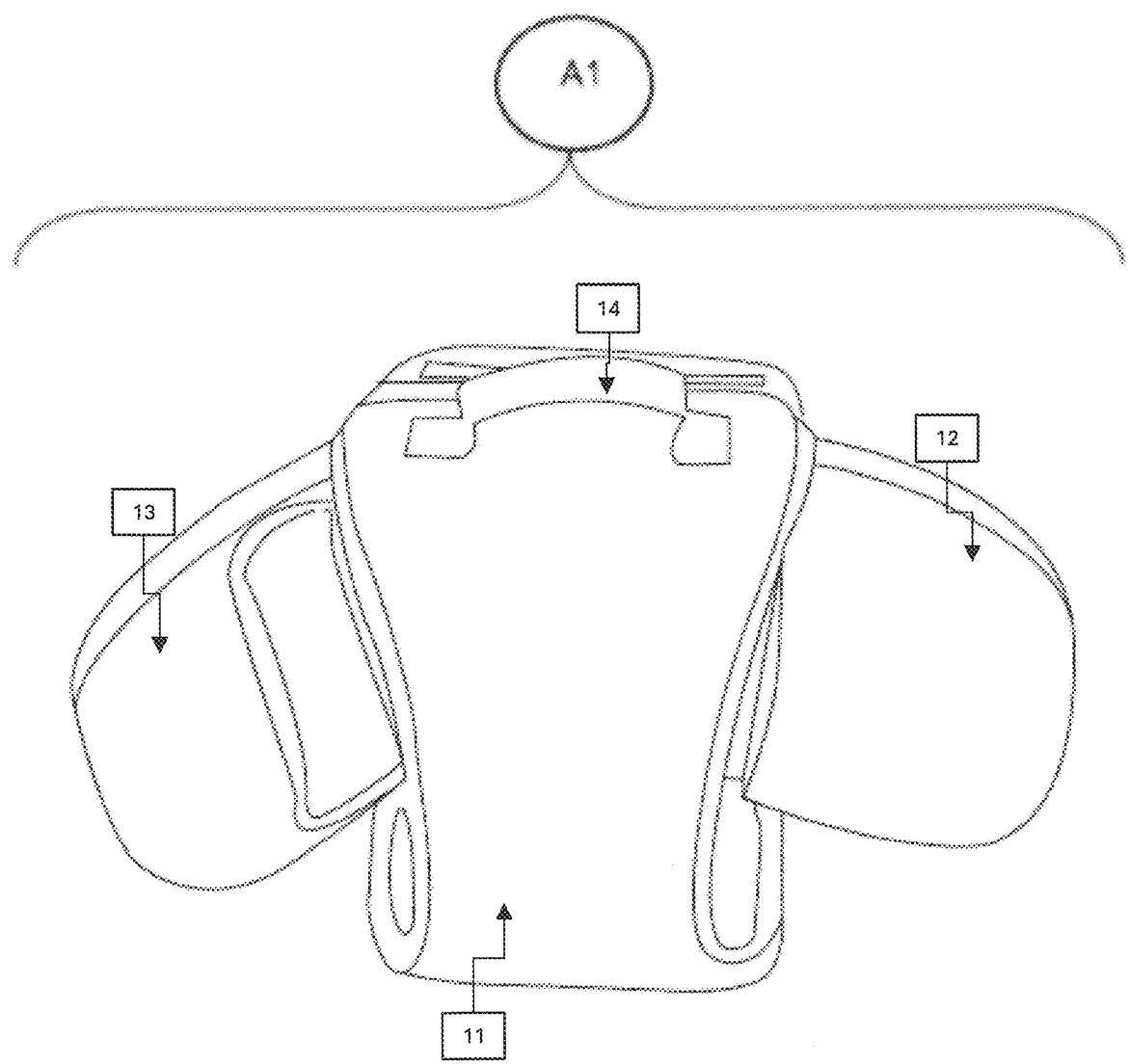
Fig. No. 29

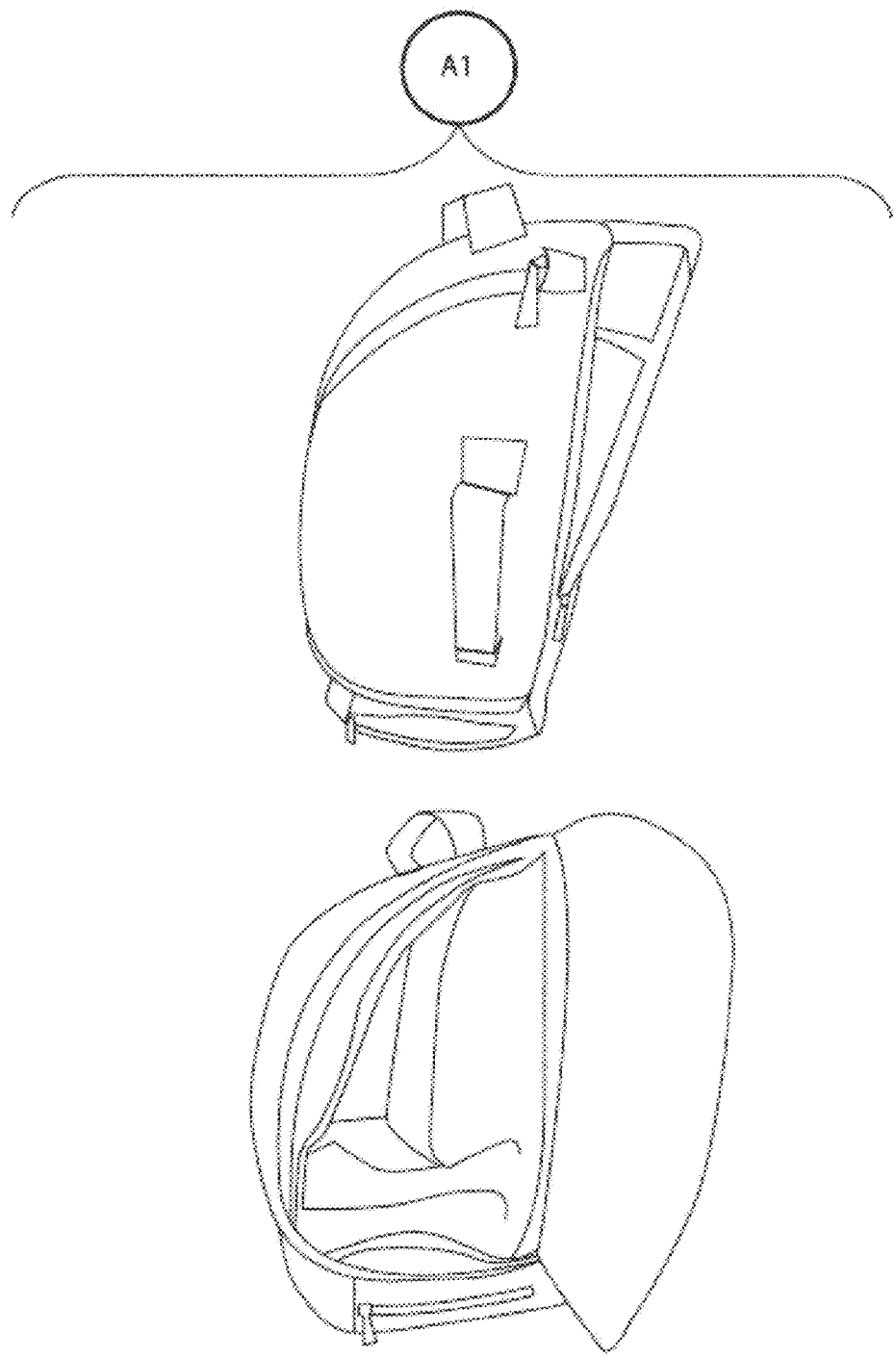
Fig. No. 30

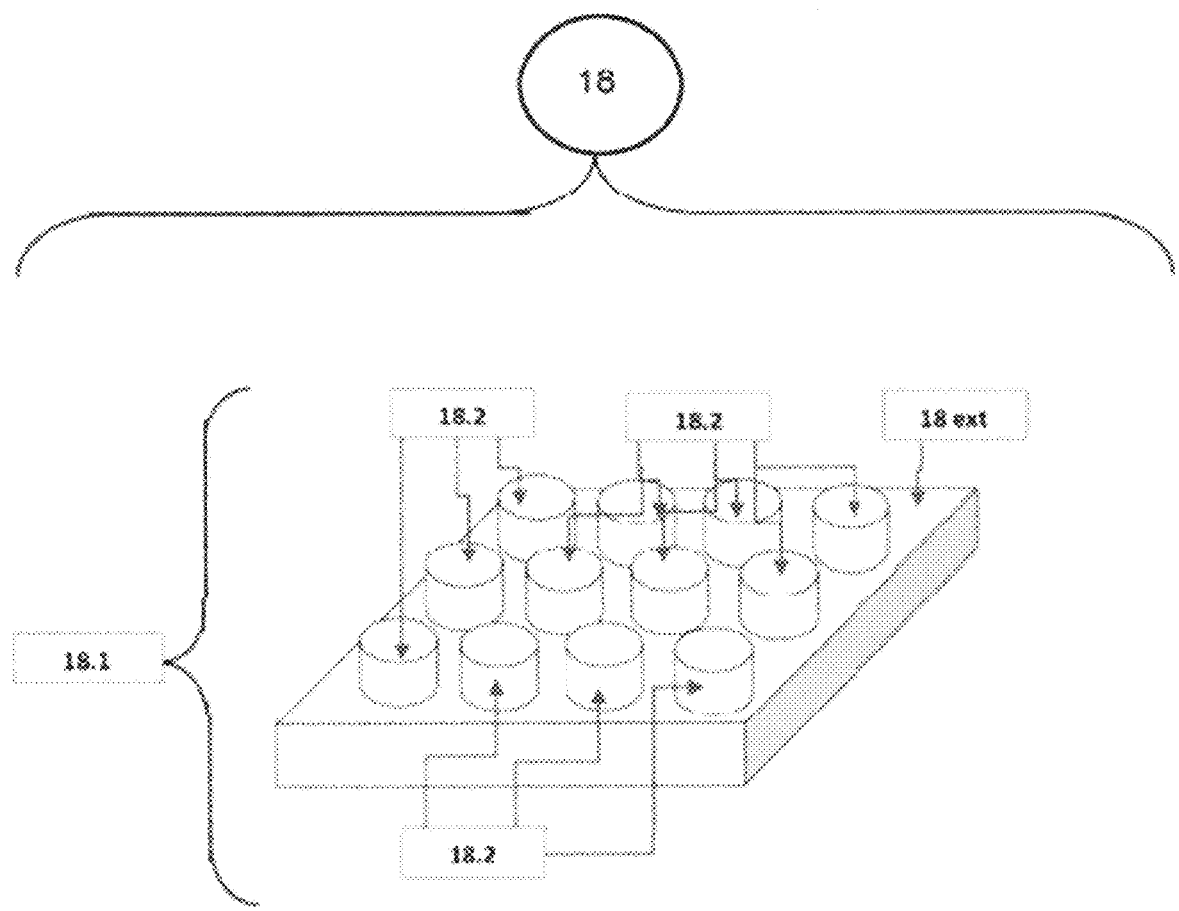
Fig. No. 31

BACKPACK FOR DOMICILIARY MEDICAL SERVICES

FIELD OF THE INVENTION

This Patent application refers to a backpack for domiciliary medical services, to optimize the transport, protection, cleaning and organization of basic medical elements (equipment and consumables) when used in patient care in each domiciliary or home visit and medical consultation by the doctor or health professional, likewise this backpack for domiciliary medical services allows easy access to medical items and personal items carried, it also provides versatility in adjustment and adaptation in each of its interior spaces according to the needs of the health care professional, in addition this backpack facilitates the cleaning and disinfection of all its inside elements by means of oxygen, UV light, water, soap, ammonium, among others, against microorganisms and bacteria that can impregnate or adhere to it. A backpack is provided for domiciliary medical services which allows a safe and effective disposal of any waste and/or hazardous waste used in the medical consultation such as syringes, gauze, tongue depressors, bandages, band-aids, etc., likewise this backpack provides to lighten the load and avoid unwanted rebounds on the back of the health professionals, which minimizes the risk of damage caused to his spine and shoulders, also this backpack simplifies its transport in confined or reduced spaces such as in public transport, avoiding disturbing other passengers or people, as it is easy to locate on the ground, on the chest or positioned laterally to one side of the health professional who carries it, in addition this bag has safety measures for its opening and, in turn, is designed in such a way that it can be unnoticed to possible threats or crime attacks when moving from one place to another or within the same mass transportation system. The backpack for domiciliary medical services allows to separate and isolate the personal objects of the physician or health professional with respect to the basic medical elements (equipment and consumables), likewise this backpack guarantees order and organization of both the basic medical elements (equipment and consumables) and of the personal elements of the doctor or health professional, allowing the disposition any of these contents by accessing and easily detecting said elements in an agile and fast way.

BACKGROUND OF THE INVENTION

Within the state of the art, there are different designs along with arrangements or constructive configurations of backpacks for domiciliary medical services, as such some documents being part of the state of the art are referenced below and can also serve as a starting point and of comparison with respect to the present invention.

The China utility patent CN 207203007 (Oct. 4, 2018) by applicant JI YUFENG [CN] describes a practical medical suitcase related to the field of medical devices. This practical medical suitcase, including the lid and the box, the top fixedly connected with the box lid latch plate, the upper part fixedly connected with the latch plate handle, the positive middle part fixedly connected with the box lid buckle, the front of the box and the position fixedly connected with the cassette corresponding with the buckle, the positive fixedly connected with the thick bamboo bar section of the box, the inside of the thick bamboo bar section is provided with the bar, the leather depository is two sets of, and two sets of leather depositories are located on both sides of the depository, respectively, and configured with the despository axis is symmetrical. This practical medical suitcase, the weight is lighter, agile and easy to carry, and the surface base has a pull rod, and the rotating wheel is furnished with the bottom, and can exchange and make the pull rod pull more medicine, saving labor and time, the Leather packing storage tank which has a foam cushion posed inside, can protect important fragile medicine, prevent due to medicine problem affecting treatment.

In the Chinese Utility Model Patent CN206596756 (Oct. 31, 2017) by the applicant JIA CUIJU [CN], it describes a utility model consisting of a multifunctional suitcase for pediatric inspection, including the first box, both sides are connected with the lever dead around the left and right sides of the body cavity, only the baffle has been evenly palisade on the outside of the dead lever surface, the first spring has been hinged on the right side of the dead lever, the activated carbon sheet is installed at the lower end of the second box, the inner chamber of the second box is equipped with the matter storage lattice, the second lower box has a mobile mounting end the moisture used to adsorb in the first box and the second box and peculiar smell activated carbon sheet, can be suitable for protection of medical instruments and medicines, prevent their oxidative corrosion, used to place the cotton between the baffle, items to use as a gauze, and the width between the baffle is adjustable, can meet different models of cotton clothing, depositing articles to use as a gauze, the end of the upper cover has the stopper which is used to prevent the article from moving in the matter storage lattice through the spacer slot and the second spring-loaded mount, that is suitable for the protection of fragile objects, so an invention with practical value is evidenced.

In China Utility Model Patent CN204861653 (Dec. 16, 2016) by Applicant YANG SHUMEI [CN], it describes a portable medical suitcase related to the technical field of infectious department medical equipment. Includes the box, and the handle is fixed with the fixed plate on the box, the handle is located on the upper surface of the box and with the fixed plate connection, the upper surface of the box is equipped with the recess and the outer box is equipped with the cover, and the bottom of the box and the lower part of the cover are connected through the cooperation of the pivot, and the upper part of the cover is equipped with retainers, the complex of the recess is fixed, and the knot is connected to the cover through the cooperation of the pivot, and the upper surface is equipped with an ultraviolet lamp in the box, and the right flank is equipped with the flat table in the box, the left surface is equipped with a foraminifera support in the box, a Dull and stereotyped end is equipped with the conductive bar and the box side is equipped with the spout. The utility model reveals a simple structure, convenient for use, make things convenient for the work of medical and nursing staff work, relieve the workload that can disinfect the medical equipment of placing in the box.

In the China Utility model patent CN204158591 (Feb. 18, 2015) by applicant HANGZHOU CHAORE TECHNOLOGY CO LTD [CN], describes a medical suitcase and belongs to the field of medical devices and instruments. One person can carry the medical bag conveniently with labor saved. The medical bag comprises a box body, a box cover, and a plurality of hinges. The cover of the box is in rotary connection with the body of the box through the hinges that are distributed on the back of the suitcase. One end of each hinge is attached to the rear face of the box body. The other end of each hinge is attached to the rear face of the case cover. A handle is fixed on the front face of the box body. One of the ends, placed on the body of the box, of the hinges is provided with bent sides that bend towards out away from the rear face of the box body. Connection holes are formed on the bent sides. Two rear belts are arranged in the suitcase. The two ends of each back belt are provided with hook buckles respectively. One of the ends of the back straps is fastened to the handle through the hook buckles. The other ends of the back straps are fastened to the folded sides through the hook buckles. The two rear belts are arranged, the person can carry the suitcase on the back by both shoulders, so that labor is saved when the person carries the suitcase, and the moving speed of the person can be high.

In the Chinese Utility Model Patent CN202554281 (Nov. 28, 2012) of the applicant AIPURUISI BEIJING BIOLOG TECHNOLOGY CO LTD [CN], describes a medical suitcase. The medical suitcase is a cuboid box body, and it is formed by a hinge of a front box body and a rear box body through a hinge. A carrying handle is arranged on the upper surface of the box body. A shackle is provided on each of the two sides of the carrying handle. Four footpads are arranged at the bottom of the box body. A layer of heat preservation velvet pad is composed on the inner wall of the box body. The medical suitcase is simple in structure, easy to fold and unfold, high in use efficiency and has a large internal storage space; and when the medical suitcase is used, the medical supplies placed in the box body are fully exposed, can be conveniently taken and placed, and mixed with difficulty.

In the U.S. Pat. No. 5,848,700 (Dec. 15, 1998) by Applicant HORN, NATHANIEL [US], describes an invention consisting of disclosing an emergency medical kit including a carrying case approximately the size of a briefcase or small suitcase with the upper and lower sections divided into many compartments by inserting a plastic organizer. Each compartment addresses a particular medical emergency, which is identified in the lid. The reverse side of the compartment cover has instructions for dealing with the emergency, while the compartment contains the care items needed for that emergency. A divider snaps along the top section of the case to help contain the contents and provides instructions for kit use, general first aid information and a list of emergency phone numbers.

GENERAL AND DETAILED DESCRIPTION OF THE INVENTION

The objective technical problem of this application is to avoid mistreatment, deterioration and destruction of basic medical elements (equipment and consumables) in their transport and transfer when the home visit and medical consultation is carried out by the doctor or professional of health, in turn those costs are reduced considerably due to losses in said basic medical elements, as well prevent disorder and waste of time looking for medical instruments and equipment along with consumable elements inside the backpack that will be used in patient care in the home medical consultation, also avoid contamination by microorganisms and bacteria both of the elements basic medical equipment (equipment and consumables) as well as the internal and external elements that make up the entire suitcase and at the same time avoid any type of pathological risk of contagion by infectious biosanitary hazardous waste such as syringes, gauze, tongue depressors, bandages, Band-Aids, etc., that are used in the home medical consultation, then minimize the risk of back injuries, of the spine and shoulders of the health professional who is going to carry out the home medical consultation, in addition to facilitating the transport and transfer of basic medical elements inside a backpack in confined or reduced spaces, avoiding inconvenience to the people around them, arranging it in locations with reduced spaces or arranged in a balanced way on the same health professional, also separating and isolating the objects personal information of the doctor or health professional with respect to basic medical elements (equipment and consumables), and finally, to avoid possible theft or criminal attacks when moving from one place to another in a public place or within a mass transportation system.

The purpose of this Invention patent is to provide the solution to the problem 35 through a backpack for domiciliary medical services to optimize the transport, protection, cleaning and order of basic medical elements (equipment and consumables) when used in patient care in their respective visit and home medical consultation by the doctor or health professional, this backpack for domiciliary medical services also allows easy access to the elements 40 medical and personal items that are transported, it also provides versatility in the adjustment and adaptation in each of its interior spaces according to the need of the health professional, in addition this backpack facilitates its cleaning and disinfection in all its elements that integrate it in its interior by means of oxygen, UV light, water, soap, ammonia, among others, against microorganisms and bacteria that can impregnate or adhere to it. A backpack is provided for domiciliary medical services which allows a safe and effective disposal of waste and/or hazardous waste used in the medical consultation such as syringes, gauze, tongue depressors, bandages, band-aids, etc., this backpack also provides lighten the load and avoid unwanted rebounds on the back of the health professional, which minimizes the risk on the damage caused to your spine and shoulders, this backpack also facilitates its transport in confined or reduced spaces such as mass public transport, avoiding bothering other passengers or people, disposing of it in the easiest way possible on the floor, on the chest or positioned laterally to the side of the health professional who transfers it.

In addition, this backpack has security measures for its opening and, in turn, is designed so that it goes unnoticed to possible threats or criminal attacks when it is moved from one place to another or within the same mass transport system. The backpack for domiciliary medical services has the power to separate and isolate the personal belongings of the doctor or health professional with respect to the basic medical elements (equipment and consumables), likewise this backpack guarantees the order of both the basic medical elements (equipment and consumables) and the personal elements of the doctor or health professional, allowing their content to be disposed of by easily accessing and observing said items quickly and easily.

The cited prior art documents, part of the state-of-the-art of the same technological field of the application is disclosed, as observed in the Chinese patents CN207203007, CN206596756, CN204861653, CN204158591, CN202554281, and in U.S. Pat. No. 5,848,700.

Based on the foregoing, said documents are referenced, in order to expose the background of the application and consider such documents as a starting point the relevant structural changes that make the application different through its constructive technical characteristics that solve the technical problem of the application.

The present invention arose due to an investigation in the improvement and innovation in the provision of medical services at home of the company of Seguros Bolivar S.A., in which considerable time and resources were spent in the research, development and innovation of the invention, considering many relevant points during its development to make a comprehensive proposal. The principle of the present invention refers to the solution of an integral objective technical problem that is currently found in the delivery of domiciliary medical services and that consists of avoiding mistreatment, deterioration and destruction of the basic medical elements in their transport and transfer, reduce costs considerably due to losses of said basic medical elements, the mix-up and waste of time looking for instruments, medical equipment and consumable items inside the suitcase, avoid contamination by microorganisms and bacteria of basic medical elements, as well as the internal and external elements that make up the backpack, avoid any type of pathological risk of contagion by hazardous infectious bio sanitary waste, minimize the risk of back, spine and shoulder injuries of the health professional, facilitate the transport and transfer of basic medical elements inside a backpack in confined or reduced spaces, greater availability of location in reduced spaces and disposed in a balanced way on the same health professional, avoid possible robberies or criminal attacks when moves from one place to another, where said problem is to be solved, by means of a backpack (1) for domiciliary medical services in which the transfer of instruments, medical equipment and consumables is optimally improved, agile, transportable and safe performing better patient care when the home visit and medical consultation is carried out by the doctor or health professional.

The present Invention refers to a backpack (1) for domiciliary medical services where several fundamental aspects and experiences during its research and development were considered, in order to obtain an optimal, such as:

- The current backpacks or suitcases for doctors are too big, where said suitcases are the same or similar to the suitcases of people who perform other domiciliary services, these backpacks or suitcases are not practical.
- The material of the backpacks or suitcases deteriorates easily, they are not hygienic, they scratch a lot, they have a dirty appearance and an old appearance.
- The current backpacks or suitcases have plenty of space, everything moves inside and produces sounds, while the transfer process is done on foot by the person carrying the suitcase or backpack.
- The backpack or suitcase does not contemplate a defined space to organize things, in addition the things that are carried in the backpack or suitcase move a lot.
- In the backpack or suitcase there are medical devices and equipment that do not fit, on several occasions they must be accommodated in other pockets or in additional backpacks or suitcases.
- In the backpack or suitcase there are plenty of spaces, they better cover other things to carry in it, thus increasing the weight of the backpack or suitcase.
- Doctors or health professionals carry more than 9 kilos on their back.
- Some experienced doctors are perceived as medical students for the simple fact of carrying their backpack or suitcase on their back, loss credibility.
- Doctors, when transporting their respective suitcases or backpacks with all their basic medical elements when they are going to make a home visit and medical consultation and are transported in a massive public transport service, can generate inconvenience both for themselves and for the passengers around them around due to the size of the suitcase.
- The domiciliary medical service is not perceived as the most hygienic by some patients.

Based on the foregoing, the invention called backpack (1) for domiciliary medical services was conceived, which solves the previously described inconveniences and problems detected and identified by interviews and surveys with doctors and health professionals that provide domiciliary medical services, the following aspects of hygiene, health regulations, health, aspects in the comprehensive management of waste, characteristics and technical and operational qualities in its design and manufacture, as follows:

Characteristics and technical and operating qualities of the case:
- Easy access.
- Easy classification of objects (equipment, instruments, consumables, personal items) within it.
- Design of modularity and spaces.
- Extraction of modules.
- Lowering system in its support straps.
- Easy handling.
- Ratio of front and rear suspension points.
- Versatility to adjust the internal modules of the case.
- Total opening of the central compartment.
- Easy opening system.
- Easy to extract objects.
- Easy strap adjustment system.
- Fabric or textile that repels and kills microorganisms and bacteria.
- Eliminates bad odors.
- Durable, non-porous, non-absorbent material.
- Easy cleaning and disinfection.
- Arrangement for temporary storage of infectious bio sanitary waste such as sharps, anatomopathological.
- Waste management in a red bag for each doctor and Health Center.
- Hygiene processes.
- Cleaning with water, soap, oxygen, UV light, disinfection with ammonia.
- Storage of personal items separately from basic medical items (equipment and consumables).
- The backpack must be semi-rigid and lined with polyamide, a fabric that does not absorb liquids, which repels bacteria, and must also contain removable compartments to facilitate their respective cleaning.
- Readiness to move and mobilize a backpack with medical instruments in mass public transport and that in turn obtains the facility of being able to place said backpack between the legs of the person who transports it so as not to bother anyone around them in front or behind him.
- In the home visit upon arrival and entering the patient's house, obtain the possibility of holding the backpack in such a way that it evokes the doctors of yesteryear in order to achieve the positioning and remembrance of the specialists or health professionals in the patient's mind.
- During the domiciliary visit, when arriving and entering the patient's house, the bag will be placed in front of the patient and when opening it, ensure that the instruments and/or equipment are arranged by arrangement in the consultation, such as a phonendoscope, set cleaning, tensiometer, among others, also this backpack will help the doctor because if the doctor finds a space empty you can know that some instrument or equipment is missing, also you will not spend so much time looking for the consultation instruments or equipment inside the suitcase, where such a situation is common today.
- Once the consultation is over, the waste and waste will be better disposed of in the backpack, through a container that is airtight and is isolated from the rest of the backpack, immediately after the consultation, all waste and residues will be deposited, where the doctor will later arrive at the medical center, which will open the container to dispose of biohazardous waste accordingly.

Hygiene aspects:

Hospital de Jove Foundation patient hygiene protocol: This is a hygiene protocol based on the definition of goals that constitute a culture of hygiene. This culture establishes that hygiene improves the quality of life, that it is a more individual responsibility, and that the culture of hygiene is best communicated by the exemplary performance of hygiene practices. Before any hygienic procedure emphasizes the importance of patient cooperation; highlight the importance of privacy in carrying out hygiene activities; avoid contact with air currents.

Hygiene protocol of the Colombian Police: This is a protocol of hygiene that is developed from the detailed observation of the different areas of citizen life. It seems important to us to mention it, because, from the surveillance of the actions that constitute the daily life of the citizen, it manages to determine the opportune hygiene actions that must be carried out in this life. Aspects to highlight: Washing hands always before and after going to the bathroom, eating and using a medical service and means of transport, in addition to removing bacteria, indicates to other people that one is aware of the bacteria present in these means; Always wash the supplies with which an activity is carried out, before carrying out this activity.

WHO Handwashing Protocol: This hygiene protocol is important for two reasons. The first of these is that it shows that there are hygiene cultures that are universal and not just local. The second is that hygiene procedures are linear. Aspects to be highlighted: direct contact of a dirty surface with the skin, even for a short time, dirty the skin. Therefore, these contacts must be avoided at all costs. The supplies and instruments to carry out hygiene activities should always be disposable.

Protocol for waste management: This protocol is important to mention because it handles waste that requires very strict rules in order not to contaminate the environment. In this way, by being able to apply these procedures of very strict rules in the home medical service, hygiene in this service will be better controlled.

Aspects to highlight: three different waste treatment procedures: volume reduction, elimination of waste and change of its composition (change from one state of matter to another; for example, the change from liquid to gaseous state).

Health regulations:

Resolution 2003 of 2014: The modality of the medical service that is provided is under the modality at home/domiciliary or extramural. The domiciliary service is found in the "other services" category, where various types of home care are found, as follows: acute patient, chronic patient without a ventilator, chronic patient with a ventilator, and consultation. It also establishes what equipment the doctor or health professional must carry in order to optimally provide the home service, for which the doctor or health professional must carry in his briefcase, the following:

Stethoscope
Tensiometer
Organ team
Pulse oximeter
Glucometer
Hammer
Thermometer
Meter
Healing Items Aspects in Comprehensive Waste Management:

The domiciliary health service provider is responsible for managing of the hazardous waste generated in the home consultation until its final disposal.

Bio sanitary waste is sterilized by the company to which the doctor or health professional providing the medical service belongs.

Characteristics that the container must have where the hazardous waste generated in the home consultation will be deposited, as follows:

Plastic material, rigid, waterproof, easy to clean and resistant to corrosion.

Does not allow entry or exit of unwanted things. (elements for its adequate closure).

Color code: RED

Should be washed 1 or 2 times a week

Guide label in a visible place informing of possible residues.

It must have a lid.

The characteristics of the bags to be deposited in the container for the hazardous waste generated in the home consultation must have the following particularities, as follows:

High density polyethylene.

The person in charge of collecting the waste must make a record, with the following information, as follows:

Generation area.
Residues it contains.
Date.
Shift

Biosanitary waste is that which comes into contact with organic matter, blood or body fluids, which includes the following consumables, as follows:

Gauze.
Cottons.
Dressings.
Drains.
Bandages.
Gloves.
Highlights.
Syringes.

Currently, there is a need for a solution to optimally perform patient care when a domiciliary medical consultation is carried out, which basically consists of care and transportation of material such as basic medical elements (equipment, instruments, and consumables) as well as maintaining their respective order, cleanliness, and transfer from one place to another in an ergonomic and safe manner for the person who transfers said items. medical elements and to better dispose wastes and final bio sanitary residues, produced after the consultation, for such need the backpack (1) for domiciliary medical services comprises an integral disposition that solves in a novel way all the previously mentioned functionalities, where the backpack (1) for domiciliary medical services is made of several components or elements solving the technical problem.

Based on the foregoing, the purpose of this Invention is to protect a backpack (1) for domiciliary medical services that is made of a main body (10), a base (20) and a load distribution system (30). The main body (10) of the backpack (1) for domiciliary medical services is made of the following essential structural components: a body (11), a right side pocket (12), a left side pocket (13), an upper handle (14), a right side handle (15), several anti-theft zippers (16), a removable compartment (17), several supports or studs (18), an elastic interlocking woven panel (19), three pockets for mobile (19 A), a large pocket (19 A.1) and a PC pocket (19 B); the base (20) of the backpack (1) for domiciliary medical services is made, as well, of the following essential structural components: a side pocket (20 A), a side pocket (20 B), a waste container (21), an auxiliary side container (22), a safety zipper (23) and a safety bag with snaps (24) and finally the load distribution system (30) comprises the following essential structural components: two adjustable vertical straps (31), an adjustable belt (32) and a padded back support (33). (See FIGS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31).

The main body (10) is made of a body (11) which is made of 600 canvas textile material with PVC coating on the outside and on the inside has ferrini textile material; The body (11) is made of a single unit that has a geometric volumetric pyramidal truncated shape (11.1) that projects towards its front, likewise on its back (11post) it has a large rectangular wall (11.2) and on the back bottom (11inf) comprises a small rectangular wall (11.3) which acts as the base of the body (11) and which, in turn, said small rectangular wall (11.3) has two small side walls (11.3.1, 11.3.2) on each of its sides (11right, 11left), likewise this body (11) comprises on its lateral sides (11right, 11left) with two openings in the form of letter D (11.4, 11.5), likewise in the opening in the form of letter D (11.4) located on the right lateral side (11der) of the body (11) it comprises two elongated tabs inside (11.6, 11.7) one of them located on the same D-shaped opening taking a curved shape and the other flange (11.7) is located and positioned vertically on the rectangular wall (11.2) in the back (11post) of the body (11), each of said elongated tabs (11.6, 11.7) has five snaps (11.6.1, 11.7.1) central from each other and located along said tabs (11.6, 11.7), finally this body (11) has inside a letter D-shaped wall (11.8) that allows dividing, isolating and separating the backpack (1) between two large compartments inside, said letter D-shaped wall (11.8) comprises a Velcro band (11.8.1) positioned horizontally and located in the middle of the wall in the form of the letter D (11.8), said Velcro band (11.8.1) is a joining element. (See FIGS. 1A, 1A, 2, 3, 4 and 5).

The right side pocket (12) is made of 600 canvas textile material with PVC coating; The right side pocket (12) is made of an opening in the shape of the letter D (11.4) of the body (11), likewise this right side pocket (12) has an outer cover (12.1) in the form of the letter D, in turn this cover (12.1) on its outer surface (12.ext) has a right side handle (15) assembled at a central distance located vertically, also such right side pocket (12) for closing and opening on its respective outer cover (12.1), comprising an anti-theft zipper (16) on its outer edge (12.1ext). (See FIG. 6).

The left side pocket (13) is made of 600 canvas textile material with PVC coating; The left side pocket (13) is made of an opening in the shape of the letter D (11.5) of the body (11), likewise this left side pocket (13) has an outer cover (13.1) in the shape of the letter D, in turn this cover (13.1) on its outer surface (13.ext) has a small pocket in the shape of the letter D (13.1.1) in a vertical position and located on the middle part (13.med) of said cover (13.1), said small pocket in the shape of the letter D (13.1.1) comprises an outer cover (13.1.1.1) and in turn includes an anti-theft zipper (16) for its opening and closing, likewise this small pocket in the shape of the letter D (13.1.1) has a pocket inside (13.1.2) and an internal separating wall (13.1.3) made of ferrini textile material; The left side pocket (13) for closing and opening on its respective outer cover (13.1) comprises an anti-theft zipper (16) on its outer edge (13.1ext). (See FIG. 7).

The upper handle (14) is made of a polyester textile material; the upper handle (14) is made of an elongated longitudinal body (14.1) which in turn has a reinforcing sheath (14.2), said reinforcing sheath (14.2) the elongated longitudinal body (14.1) is inserted inside this assembly between these two parts is intended to achieve the greatest resistance when used as a support point so that the user can lift or carry the backpack (1) for domiciliary medical services without any detachment from it. The elongated longitudinal body (14.1) of the upper handle (14) is located in the upper part and assembled by means of resistant threads and seams in a horizontal position on the outer part (11.ext) of the body (11) that forms the main body (10) of the backpack (1). (See FIG. 8).

The right-side handle (15) is made of a polyester textile material; the right-side handle (15) is made of an elongated longitudinal body (15.1) which, in turn, has a reinforcing sheath (15.2), said reinforcing sheath (15.2) is inserted inside into the elongated longitudinal body (15.1). This assembly between these two parts is intended to achieve greater resistance when used as a support point so that the user can lift or carry the backpack (1) for domiciliary medical services without there being some detachment from it. The elongated longitudinal body (15.1) of the right lateral handle (15) is located on the lateral part right and assembled by means of resistant threads and seams in a vertical position on the outer surface (12.ext) of the outer cover (12.1) of the right-side pocket (12) of the body (11) that forms the main body (10) of the backpack (1). (See FIG. 9).

The anti-theft zipper (16), is made of a polyester textile material and steel, bronze and/or brass; The anti-theft zipper (16) is made of a tape (16.1) that is made of two parallel strips (16.1a, 16.1b), which on each of its edges (16.1a", 16.1b') comprise teeth (16.2) interleaved made of plastic, nylon or metal, the union or opening of each of the teeth (16.2) are joined or opened by the passage of a sliding head (16.3), likewise this anti-theft zipper (16) has an internal lip (16.4) and an external lip (16.5) in order to protect the zipper of possible attacks or violations of the opening of the zipper (16) to prevent the opening of the backpack (1) for domiciliary medical services. (See FIG. 10).

The removable compartment (17) is made of a ferrini textile material; The perimeter exterior (17.2) comprising an elongated rectangular wall (17.2.1) in its rear removable compartment (17) includes a body (17.1) that is made of a panel (17.post), also comprising an elongated wall in the form of letter D (17.2.2) in its front part (17.front) and extending over its lateral parts (17.der, 17.izq) and also has an elongated wall in the shape of the letter D (17.2.3) in its lower part (17. inf) which conforms a base, in said wall (17.2.3) in its middle part it has a Velcro (17.2.3.1) located horizontally as a means of union. The removable compartment (17) inside has several dividing panels which has two small rectangular horizontal dividing panels (17.3.1, 17.3.2) and two vertical dividing panels, one small (17.4.1) that has a Velcro strap (17.4.1.1) and one large (17.4.2), each of these dividing panels (17.3.1, 17.3.2, 17.4.1, 17.4.2) on each of their respective outer edges (17.3.1',17.3.2',17.4.1',17.4.2')

have Velcro joints (17.3", 17.4") which can be easily removed and installed, forming new spaces to place equipment or instruments when required according to the need of the physician or health professional and, at the same time, can be easily cleaned and disinfected. On the back (17.post) of the outer perimeter panel (17.2) of the removable compartment (17) there is an elongated horizontal tab (17.2.3) located at the top of the elongated rectangular wall (17.2.1) which has five snaps (17.2.3.1) that are located central from each other, also on the front (17.front) of the outer perimeter panel (17.2) of the removable compartment (17) comprises another elongated horizontal flange (17.2.3) located in the upper part of the elongated wall in the form of the letter D (17.2.2) which has five clasps (17.2.3.1) that are located central from each other, said clips (17.2.3.1) are intended to have a point of attachment and support of the removable compartment (17) on the body (11) of the main body (10) of the backpack (1) providing it with the characteristic of removing and reinstalling said removable compartment (17) when required. This removable compartment (17) has a special pocket (17.5) which is part of the large vertical dividing panel (17.4.2), this pocket on the inside has a simple handle (17.5.1) as a support point to hoist or lift the removable compartment (17), likewise said special pocket (17.5) is in order to store important documents that are used in home medical consultation and it is also used to store electronic devices such as electronic tablets, among others (See FIGS. 11 and 31).

The support or stud (18) is made of rubber or plastic material resistant to loads and friction wear; The support or stud (18) has a large rectangular body (18.1) that has a considerable thickness, likewise this body large rectangular (18.1) on its outer surface (18.ext) has several triangular or cylindrical protrusions (18.2) aligned with each other, said protrusions (18.2) are intended to support the weight of the backpack (1) when the backpack (1) is arranged on a surface or place and also has the purpose of resisting wear and abrasion when the backpack (1) is moved. In the backpack (1) for domiciliary medical services assembles at its base (20) by means of stitching, rivets or by heat four (4) supports or studs (18) located equidistantly on the base (20) to balance the weight of the backpack (1). (See FIG. 31).

The elastic interlocking woven panel (19) is made of a ferrini textile material and elastic textile material; The elastic interlocking woven panel (19) is made of a rectangular body (19.1) of medium size that has a rectangular structural panel (19.1.1), said body (19.1) is also made of several elastic bands (19.1.2, 19.1.3) woven together, in which said tapes (19.1.2, 19.1.3) are positioned horizontally and vertically, thus forming a fabric. This the elastic interlocking woven panel (19) has a velcro strap (19.2) located horizontally in the middle part of the elastic interlaced woven panel (19) on its back (19.post). Said velcro strap (19.2) is for the purpose that it can be adhered or adjusted to the interior of the special pocket (17.5) of the removable compartment (17) likewise said elastic interlaced woven panel (19) is used to adjust and adhere documents, instruments, equipment or other objects that are necessary for their respective carrying by the doctor or health professional, in addition said elastic interlocking woven panel (19) is located inside the special pocket (17.5) of the removable compartment (17) of the spaces of the removable compartment (17). (See FIG. 12). The mobile pocket (19 A) is made of neoprene textile material; The cell phone pocket (19 A) is made of a single body (19 A.1) that has a semi-curved vertical side shape, this cell phone pocket (19 A) that has its body (19 A.1) has its sides sides (19 A.1.1, 19 A.1.2) and its lower base (19 A.1.3), said lateral sides (19 A.1.1, 19 A.1.2) and its lower base (19 A.1.3) are joined via of thread seams on the inside of the rectangular wall (11.2) of the body (11) of the main body (10) of the backpack (1) for domiciliary medical services. (See FIG. 13).

The large pocket (19 A.1) is made of neoprene textile material; The pocketcell phone pocket (19 A) that has its body (19 A.1.1) has its lateral sides (19 A.1.1.1, 19 A.1.2.1) and its lower base (19 A.1.3.1), said lateral sides (19 A.1.1.1, 19 A.1.2.1) and its lower base (19 A.1.3.1) is joined by thread seams on the inside and in the middle of the wall in the form of letter D (11.8) of the body (11) of the main body (10) of the backpack (1) for domiciliary medical services. (See FIG. 14).

The PC pocket (19 B) is made of ferrini textile material; The pocket for PC holder (19 B) comprises a single large rectangular body (19 B.1.1) acquiring the same shape of the large rectangular wall (11.2) of the body (11), also said large rectangular body (19 B.1.1) has two joined surfaces (19 B.1.1.1, 19B1.1.2) together forming the pocket (19 B), also on the upper edges (19 B.1.1.1', 19B1.1.2") in the upper area (19 B sup) of the two surfaces (19 B.1.1.1, 19B1.1.2) until its middle area (19 B med) has an anti-theft zipper (16) for their respective opening and closing in order to insert or remove the electronic device, in this case the PC, also from the middle area (19 B mid) to the lower area (19B inf) of the two surfaces (19 B.1.1.1, 19B1.1.2) of the body (19 B.1.1) of the pocket (19 B) are joined by thread seams. The PC holder pocket (19 B) is joined by thread seams to the large rectangular wall (11.2) of the body (11) of the main body (10) of the backpack (1) for domiciliary medical services. The PC pocket (19 B) also has two internal rectangular pockets, one large (19B.2) and the other small (19B.3), said small pocket (19B.3) is on the upper surface of the large size pocket (19B.2). (See FIG. 15).

The side pocket (20 A) is made of ferrini textile material; The side pocket (20 A) comprises a single body (20 A.1) that includes a square horizontal side shape, this side pocket (20 A) has two joined surfaces (20 A.1.1.1, 20 A1.1.2) to each other by means of thread seams forming the pocket (20 A), also on the edges upper (20 A.1.1.1', 20 A1.1.2') in the upper area (20 A sup) of the two surfaces (20 A.1.1.1, 20 A1.1.2) of the body (20 A.1) have a safety zipper (23) for their respective opening and closing in order to insert or remove the waste container (21). The side pocket (20 A) is joined by means of thread seams to the small side wall (11.3.1) that is part of the side wall (11.3) that acts as the base of the pocket body (11) of the main body (10) of the backpack (1) for domiciliary medical services. (See FIG. 16).

The waste container (21) is made of plastic and thermoplastic material; The waste container (21) is made of a single rigid box-shaped body elongated (21.1) which has six lateral faces (21.1.1, 21.1.2, 21.1.3, 21.1.4, 21.1.5, 21.1.6) and on its lateral face (21.1.6) there is an opening (21.1.6.1) to introduce or remove the security bag with snaps (24). The waste container (21) also has a lining (21.2) in nylon or neoprene fabric with the same shape as its rigid body (21.1), where said lining (21.2) has several snaps (21.2.1) equidistant from each other and located towards the lateral opening (21.1.6.1) of the lateral face (21.1.6) of the waste container (21), these snaps (21.2.1) of the lining (21.2) of the waste container (21) is for the purpose of holding and/or separating the security bag with snaps (24) in order to carry out the activity of depositing the bio sanitary waste and in addition to carrying out its respective cleaning and disinfection. (See FIGS. 15 17).

The side pocket (20 B) is made of ferrini textile material; The side pocket (20 B) is conforms of a only Body (20 B.1) that have a form side horizontal square, this side pocket (20 B) has two surfaces joined (20 B.1.1.1, 20 B1.1.2) to each other by means of thread seams forming the pocket (20 B), also on the upper edges (20 B.1.1.1', 20 B1.1.2') in the zone higher (20 B. His p) of the two surfaces (20 B.1.1.1, 20 B1.1.2) of Body (20 B.1) comprises a zipper of security (23) for their respective opening and closing to insert or remove the side umbrella container (22). The side pocket (20 B) is attached by thread seams to the small wall side (11.3.1) that does part of the wall side (11.3) that does of base of the body (11) of the main body (10) of the backpack (1) for domiciliary medical services. The side pocket (20B) is located on the left side of the backpack (1) and adjacent to the side pocket (20 A) located in the part right side of backpack (1). The side pocket (20B) has the same structural configuration as the side pocket (20A), the only difference it is that the left side pocket (20B) is adjacent to the other pocket (20A) located on the right side of the backpack (1). (See FIG. 16).

The auxiliary side container (22), is made of plastic and thermoplastic material; The lateral umbrella container (22) is made of a single rigid body in the form of an elongated box (22.1) which comprises six lateral faces (22.1.1, 22.1.2, 22.1.3, 22.1.4, 22.1.5, 22.1.6) and on its lateral face (22.1.6) there is a lateral opening (22.1.6.1) with the finish of Introduce either take objects that require. The container side assistant (22) also comprises a lining (21.2) in nylon or neoprene fabric with the same shape as its rigid body (21.1). (See FIG. 18).

The safety zipper (23), is made of a polyester textile material and steel, bronze me brass; The safety zipper (23) is composed of a headband (23.1) which includes two parallel strips (23.1a, 23.1b), which on each of its edges (23.1a', 23.1b') comprises interleaved teeth (23.2) that can be made of plastic, nylon or metal, the union or opening of each of the teeth (23.2) are joined or opened by the passage of a sliding head (23.3), likewise this rack of security (23) comprises a lip internal (23.4) Y a lip external (23.5) to protect the zipper from a possible theft of the waste container (21) and therefore from the theft of the security bag (24). The safety zipper (23) by bio sanitary conventions must be red. (FIG. 19).

The safety bag with snaps (24) is made of polyethylene, PVC, PVDC, polyester textile material; The safety bag with snaps (24) is made of a single rectangular body (24.1) that has two joined surfaces (24.1.1, 24.1.2) Come in Yes forming the bag (24), in where since its zone higher (24 His p) until zone lower (24 inf) Y their zones sides (24 right, 24left) of each a of the two surfaces (24.1.1, 24.1.2) of the body (24.1) of the security bag with snaps (24) are joined by means of thread seams and, in turn, an upper opening is formed in its upper area (24.3). In the rectangular body (24.1) of the security bag with snaps (24) in its upper area (24 sup) it has several snaps (24.2.1) equidistant Come in Yes Y located in each a of their surfaces (24.1.1, 24.1.2) and in the upper opening (24.3) to open and/or close the security bag with snaps (24) for Introduce either subtract the bags plastic of the waste bio sanitary, in addition with said brooches (24.2.1) it has the purpose of fastening and/or separating the security bag with brooches (24) from the lining (21.2) of the waste container (21) to be able to carry out the exercise of to deposit the waste bio sanitary Y what's more of realize its respective cleaning and disinfection. (See FIG. 20).

The adjustable vertical strap (31) is made of polyester textile material; The adjustable vertical strap (31) is made of a single longitudinally elongated rectangular body (31.1) that has a wide cross section (31.1.1) which can comprise a curved or straight shape, said body (31.1) projects vertically from the upper area of the backpack (1) to the lower area of the same. The adjustable vertical strap (31) incorporates on its superior side (31 sup) a card holder pocket (31.2) that is made of neoprene and at the same time on the same upper surface (31 sup) comprises a bias or horizontal band (31.3) to anchor a holding device for a license or ID. In the adjustable vertical strap (31) in its lower area (31.inf) it comprises an adjustable strap (31.4) made of a polyester textile material, the which comprises a longitudinal elongated rectangular body (31.4.1) with a small cross section (31.4.1.1) which in turn comprises two sections (31.4', 31.4"), said adjustable strap (31.4) in its section (31.4') is attached to the adjustable vertical strap (31) in its lower area (31.sup) by means of thread seams, likewise this adjustable strap (31.4) comprises in its section (31.4') a buckle or tie (31.5) made in plastic or brass to adjust the length of the adjustable strap (31.4), such buckle (31.5) unites the section (31.4') with the end of the section (31.4") which in turn joins in its other end by means of thread seams to a triangular tab (11.6) that is attached to the lower lateral part of the backpack (1) for domiciliary medical services. (See FIG. 21).

The adjustable belt (32) is made in a polyester textile material; The adjustable belt (32) comprises an adjustable strap (32.1) made of a polyester textile material, which comprises an elongated rectangular longitudinal body (32.1.1) with a small cross section (32.1.1.1) which, in turn, is located in two sections (32.1', 32.1"), said adjustable strap (32.1) in its section (32.1') at one of its ends is united through seams of thread to the right side half part of the backpack (1) and at its other end of said section (32.1') has a male-type plastic fitting (32.1'.2) in which said section (32.1') is interlocked and secure to said fitting (32.1'.2), also in its other section (32.1") in one of its ends is united through seams of thread to the left side half part of backpack (1) and in its other end of the other section (32.1") to a female-type plastic fitting (32.1".2) in which said section (32.1") is interlocked and secure to said fitting (32.1".2). The sections (32.1', 32.1") that make up the adjustable strap (32.1) can be adjusted and/or opened by means of their fittings (32.1'.2, 32.1".2) to adjust and balance the weight of the backpack (1) to the user who is carrying it. (See FIG. 22).

The padded back support (33) is made in polyester textile material and with foamed material; the padded back support (33) has a single rectangular body (33.1) which, in turn, is made of several rectangular panels (33.1.1, 33.1.2, 33.1.3, 33.1.4) that conform the said body (33.1), said rectangular panels (33.1.1, 33.1.2, 33.1.3, 33.1.4) are adjacent to each other vertically, adopting the same large rectangular shape of the rectangular wall (11.2) of the body (11) of the main body (10) of the backpack (1). This padded back support (33) is arranged inside and adjacent to the rectangular wall (11.2) of body (11) operating as reinforcement and structural support for the any weight included in the backpack (1) and that helps to support and balance forces due to the weight that is carried in the backpack (1) providing the user with greater comfort and support when carrying it. (See FIG. 23).

The backpack (1) for domiciliary medical services conforms of a Main body (10), a base (20), and a load distribution system (30). The main body (10) is conformed by the body (11), said body (11) on its lateral sides (11right, 11left) has two openings in the form of the letter D (11.4, 11.5), each of these openings in letter D (11.4, 11.5) are joined by thread seams on the back (11.post) of their respective side pockets (12, 13), likewise both the right side pocket (12) and the left side pocket (13) at their respective outer edges and, in turn, at the outer edges of the letter D-shaped openings (11.4, 11.5) of the body (11) are assembled by means of thread seams respectively to the anti-theft zippers (16) in order to make the opening and closing of said pockets (12, 13), similarly on the same right side pocket (12) in its outer cover (12.1) on its outer surface (12.ext) has a right side handle (15) assembled by thread seams located vertically, on the same right side pocket (12) on the opening in form of letter D (11.4) located on the right lateral side (11der) of the body (11) is assembled in its inside the removable compartment (17), said removable compartment (17) is assembled and coupled by means of its snaps (17.2.3.1) found on the elongated horizontal flanges (17.2.3) with the snaps (11.6.1, 11.7.1) of the elongated flanges (11.6, 11.7) internal that are located in the opening in the form of letter D (11.4) so much in the wall rectangular (11.2) of the part later (11 post) as in the same opening (11.4) of the body (11), likewise this removable compartment (17) is also assembled by means of its Velcro band (17.2.3.1) to the band of Velcro (11.8.1) that find in the wall in form of letter D (11.8) that it is found internally in the body (11) of the main body (10) of the backpack (1) for domiciliary medical services; The removable compartment (17) is located internally within of Body (11) of Main body (10) of backpack (1), a its time fifty said removable compartment (17) has a small vertical dividing panel (17.4.1) that by means of its Velcro strap (17.4.1.1) adheres and attaches to the Velcro strap (19.2) of panel knitting intertwined elastic (19), staying said the elastic interlocking woven panel (19) positioned vertically and parallel to the small vertical partition panel (17.4.1) (FIGS. 2, 3, 4, 26, 27, 28, 29, and 30); furthermore, the assembly of the backpack (1) for domiciliary medical services, in the main body (10) which is part of the body (11) on its left lateral side (11left) has the opening in the form of letter D (11.5), in said opening in the form of letter D (11.5) comprises a respective left side pocket (13), in said left side pocket (13) on its exterior surface (13.ext) of its outer cover (13.1) has a small pocket in the shape of the letter D (13.1.1) assembled in vertical position and located on the medium part (13.med) of said outer cover (13.1), this small pocket in form of letter D (13.1.1) has an exterior cap (13.1.1.1), said exterior cap (13.1.1.1) comprises on its edge an anti-theft zipper (16) for the respective opening and closing, likewise this small pocket in form of letter D (13.1.1) also comprises internally another small pocket (13.1.2) and at the same time it has an internal separation wall (13.1.3) making this small pocket in the shape of the letter D (13.1.1) completely separate and isolated; also on the left side (11left) of the body (11) there is the same opening in form of letter D (11.5), which internally assembles by means of thread seams four pockets (19A, 19 A.1), three of these pockets (19A) are for mobile phones in vertical position, a first pocket (19A) joined by means of thread seams in the upper part of the rectangular wall (11.2) of the body (11), likewise the other two pockets (19A) are positioned vertically and overlapping one in front of other united by means of seams of thread in the lower part of the rectangular wall (11.2) of the body (11), likewise the fourth large pocket (19 A.1) is joined by thread seams on the inside and on the middle part of the wall in the form of letter D (11.8) of the body (11) of the main body (10) of backpack (1) for domiciliary medical services (See FIGS. 2, 3, 4, 5, 26, 27, 28, 29, and 30); Additionally, the backpack assembly (1) in its body (11), in its upper part (11.sup) and in its outer part (11.ext) is assembled by means of resistant threads and seams in position horizontal an upper handle (14), is used as support for the user to raise or carry the backpack (1) without any detachment, likewise on the same body (11) on its part later (11.post) and on its large rectangular wall (11.2) a PC holder pocket (19 B) is assembled by means of thread seams, this PC holder pocket (19 B) inside comprises two internal rectangular pockets, one large (19B.2) and the other one small (19B.3), said small pocket (19B.3) is found on the upper surface of large pocket (19B.2), the same PC holder pocket (19B) on its upper edges (19 B.1.1.1', 19B1.1.2") in its upper area (19 B sup) of its two surfaces (19 B.1.1.1, 19B1.1.2) up to their middle area (19 B med) have an anti-theft zipper (16) for their respective opening and closing to insert or remove the electronic device in this case the PC or laptop (See FIGS. 2, 3, 4, 5, 15, 26, 27, 28, 29, and 30).

Furthermore, the assembly of the backpack (1) in its body (11) in its lower part (11.inf) has a base (20), this base (20) comprises several elements (20A, 20B, 21, 22, 23), including a side pocket (20A) located on the right lateral side (11.der) of the body (11), this side pocket (20 A) united by means of seams of thread to a small wall side (11.3.1) that is part of the side wall (11.3) which, in turn, is part of the base of the body (11), said side pocket (20 A) on its upper borders (20 A.1.1.1', 20 A1.1.2") of their two surfaces (20 A.1.1.1, 20 A1.1.2) has a safety zipper (23) for opening and closing and to insert or remove the waste container (21), likewise such waste container (21) comprises a cloth cover (21.2) of nylon or neoprene with the same shape as its rigid body (21.1), where said lining (21.2) has several snaps (21.2.1) located in its lateral opening (21.1.6.1) of its lateral side (21.1.6), these snaps (21.2.1) of the cover (21.2) of the waste container (21) hold with the brooches (24.2.1) located in the surfaces (24.1.1, 24.1.2) of the upper opening (24.3) of the safety bag with snaps (24), likewise the snaps (21.2.1, 24.2.1) of the lining (21.2) of the waste container (21) separating and joining the safety bag with snaps (24) to deposit the bio sanitary waste and also for cleaning and disinfection.

The backpack (1) for domiciliary medical services has two layouts (A1, B1); layout (A1) focuses in a backpack (1) for domiciliary medical services which comprises in the right lateral side (11.right) of its body (11) a side pocket (20 A) together with its respective waste container (21) together with its lining (21.2) and the safety bag with snaps (24) without any other additional element on its base (20) and the other layout (B1) the backpack (1) for domiciliary medical services comprises on the left side (11.left) of its body (11) a side pocket (20 B) together with its respective auxiliary side container (22) and at the same time on its right lateral side (11.der) of the body (11) comprises the side pocket (20 A) together with its respective container (21) along with its lining (21.2) and the safety bag with snaps (24), that is, it has its two pockets (20A, 20B) at the same time along with its containers (21, 22) and the bag with snaps (24) (See FIGS. 2, 3, 4, 5, 15, 16, 20, 26, 27, 28, 29, and No. 30).

The backpack (1) for domiciliary medical services conforms of a main body (10), a base (20), and a load distribution system (30). The main body (10) is conformed by the body (11), said body (11) on its lateral sides (11right, 11left) has two openings in the form of the letter D (11.4, 11.5), each of these openings (11.4, 11.5) joined by thread seams on the back (11.post) to their respective side pockets (12, 13), likewise both the right side pocket (12) and the left side pocket (13) at their respective outer edges and, in turn, at the outer edges of the letter D-shaped openings (11.4, 11.5) of the body (11) assembled by means of thread seams respectively to anti-theft zippers (16) for opening and closing of said pockets (12, 13), similarly, the same right side pocket (12) in its outer cover (12.1) on its outer surface (12.*ext*) has a right side handle (15) assembled by thread seams located vertically, to the same right side pocket (12) on the opening in form of letter D (11.4) located on the right lateral side (11*der*) of the body (11) assembled inside the removable compartment (17), said removable compartment (17) is assembled and coupled by means of its snaps (17.2.3.1) found on the elongated horizontal flanges (17.2.3) with the snaps (11.6.1, 11.7.1) of the internal elongated flanges (11.6, 11.7) that are located in the opening in the form of letter D (11.4) and in the rectangular wall (11.2) of the backside part (11 post) as in the same opening (11.4) of the body (11), likewise this removable compartment (17) is also assembled by means of its Velcro band (17.2.3.1) to the other Velcro band (11.8.1) located in the wall in form of letter D (11.8) found internally in the body (11) of the main body (10) of the backpack (1) for domiciliary medical services; the removable compartment (17) is located internally within of body (11) of main body (10) of backpack (1), and said removable compartment (17) has a small vertical dividing panel (17.4.1) that by means of its Velcro strap (17.4.1.1) adheres and attaches to the Velcro strap (19.2) of knitting intertwined elastic panel (19), which is positioned vertically and parallel to the small vertical partition panel (17.4.1) (FIGS. 2, 3, 4, 26, 27, 28, 29, and 30); furthermore, the assembly of the backpack (1) for domiciliary medical services, in the main body (10) which is part of the body (11) on its left lateral side (11left) comprises an opening in the form of the letter D (11.5), in said opening in the form of letter D (11.5) is its respective left side pocket (13), in said left side pocket (13) on the exterior surface (13.*ext*) of its outer cover (13.1) comprising a small pocket in the shape of the letter D (13.1.1) assembled in vertical position and located on the middle part (13.*med*) of outer cover (13.1), this small pocket in form of letter D (13.1.1) have a exterior cap (13.1.1.1), said exterior cap (13.1.1.1) on its edge comprises a anti-theft zipper (16) for their respective opening and closing, likewise this small pocket in form of letter D (13.1.1) internally it also has another small pocket (13.1.2) and at the same time it has an internal separation wall (13.1.3) making this small pocket in the shape of the letter D (13.1.1) completely separate and isolated; also on the body (11) on its side stand left side (11left) in the same opening in form of letter D (11.5) are internally assembled by means of thread seams four pockets (19A, 19 A.1), firstly three of these pockets (19A) are for mobile phones in vertical position, a first pocket (19A) It is joined by means of thread seams in the upper part of the rectangular wall (11.2) of the body (11), likewise the other two pockets (19A) are positioned vertically and overlapping one in front of other united by means of seams of thread in the lower part of the rectangular wall (11.2) of the body (11), likewise the fourth large pocket (19 A.1) is joined by thread seams on the inside and on the middle part of the wall in the form of letter D (11.8) of the body (11) of the main body (10) of backpack (1) for domiciliary medical services (See FIGS. 2, 3, 4, 5, 26, 27, 28, 29, and 30); Furthermore, the backpack assembly (1) in its body (11) in its upper part (11.*sup*) and on its outer part (11.*ext*) is assembled by means of resistant threads and seams in position horizontal a handle higher (14), bliss handle (14) used as support for the user to raise or carry the backpack (1) without detachment, likewise on the same Body (11) on its part later (11.post) and on its large rectangular wall (11.2) a PC holder pocket (19 B) is joined and assembled by means of thread seams, this PC holder pocket (19 B) inside has two internal pockets one large rectangular (19B.2) and the other one small (19B.3), said small pocket (19B.3) is located on the upper surface of the large pocket (19B.2), you too This same PC holder pocket (19B) on its upper edges (19 B.1.1.1', 19B1.1.2") in its upper area (19 B sup) of its two surfaces (19 B.1.1.1, 19B1.1.2) up to their middle area (19 B med) have an anti-theft zipper (16) for their respective opening and closing in order to insert or remove the electronic device in this case the PC or laptop (See FIGS. 2, 3, 4, 5, 15, 26, 27, 28, 29, and 30). Furthermore, the assembly of the backpack (1) in its body (11) in its lower part (11.*inf*) it has a base (20), this base (20) has several elements (20A, 20B, 21, 22, 23) that make it up, including a side pocket (20A) located on the right lateral side (11.*der*) of the body (11), this side pocket (20 A) united by means of seams of thread a small wall side (11.3.1) that is part of the side wall (11.3) which in turn is part of the base of the body (11), said side pocket (20 A) on borders superiors (20 A.1.1.1', 20 A1.1.2") of their two surfaces (20 A.1.1.1, 20 A1.1.2) has a safety zipper (23) to their respective opening and closing in order to insert or remove the waste container (21), likewise This container of waste (20-one) comprises a cover (21.2) in cloth of nylon or neoprene with the same shape as its rigid body (21.1), where said lining (21.2) has several snaps (21.2.1) located in its lateral opening (21.1.6.1) of its expensive side (21.1.6), these brooches (21.2.1) of cover (21.2) of container of waste (20-one) couple Y hold with the brooches (24.2.1) located in the surfaces (24.1.1, 24.1.2) of the upper opening (24.3) of the security bag with snaps (24), likewise the snaps (21.2.1, 24.2.1) of the lining (21.2) of the waste container (21) have the purpose of separating and joining the security bag with snaps (24) to deposit the bio sanitary waste and also carry out its respective cleaning and disinfection. The backpack (1) for domiciliary medical services has two layouts (A1, B1), the layout (A1) focus in that it is a backpack (1) for domiciliary medical services items which on the right lateral side (11.right) of its body (11) has a side pocket (20 A) together with its respective waste container (21) together with its lining (21.2) and the security bag with brooches (24) without any other additional element on its base (20) and the other provision (B1) is a backpack (1) for domiciliary medical services the which on side stand left side (11.left) of its Body (11) have a side pocket (20 B) together with its respective auxiliary side container (22) and at the same time on its right lateral side (11.*der*) of the body (11) has the side pocket (20 A) together with its respective container (21) along with its lining (21.2) and the safety bag with snaps (24), that is, it has its two pockets (20A, 20B) at the same time along with its containers (21, 22) and the bag with brooches (24) (See FIGS. 2, 3, 4, 5, 15, 16, 20, 26, 27, 28, 29, and 30).

Furthermore, the assemble of backpack (1), in the right lateral side (11.*der*) of the body (11) a side pocket (20 A) is assembled and united by means of seams of thread to a small side wall (11.3.1) being part of the wall side (11.3) that is part, in turn, of the base of the same body (11), said lateral pocket (20A) on its upper edges (20 A.1.1.1', 20 A1.1.2") of its two surfaces (20 A.1.1.1, 20 A1.1.2) comprises a safety zipper (23) for its respective opening and closing to introduce or take the auxiliary side container (22), said side pocket (20B) is located on the left side of backpack (1) and adjacent to the side pocket (20 A) located in the right side part side of the backpack (1) conforming the arrangement (B1) (See FIGS. 2, 3, 4, 5, 15, 16, 20, 26, 27, 28, 29, and 30), also in said body (11) in its lower part (11.*inf*) a small rectangular wall (11.3) is located, which conforms part of the base of body (11), is wall rectangular small (11.3) is joined by thread seams to the pockets (20A, 20B) of the base

(20) of the backpack (1), also the base (20) and the small rectangular wall (11.3) make a single element for layout (A1) of the backpack (1) and for the layout (B1) of the backpack (1) the base (20) and the small rectangular wall (11.3) are adjacent one below the other, that is, the small rectangular wall (11.3) is located firstly and next in vertical position the base (20) together with its respective comprising elements (20A, 20B, 21, 22, 23), likewise in the backpack (1) for domiciliary medical services in each of its layouts (A1, B1) is assembled both in the small rectangular wall (11.3) of the body (11) as in the base (20) by means of seams, rivets or by heating to four (4) supports or studs (18) located equidistantly on the base (20) or on the small rectangular wall (11.3) of the body (11) to balance the weight of the backpack (1) on a certain surface (See FIGS. 24, 25, 26, 27, 28, 29, 27, 28, 29, and 30).

Furthermore, the assemble of backpack (1) in its body (11) in its backside part (11.post) has a load distribution system (30), this system (30) comprises several items (31, 32, 33), among them two adjustable vertical straps (31) which are located between each other, each one adjacent to the other on each of the lateral sides (11der, 11left) of Body (11) of the backpack (1), said adjustable vertical straps (31) are assembled to the body (11) of the backpack (1) by means of thread seams from the upper part (11.sup) of said body (11) and, in turn, these same adjustable vertical straps (31), which have adjustable straps (31.4) are attached in their ends through seams of thread to triangular tabs (11.6) which are joined at the lower lateral part on each of the lateral sides (11right, 11izq) of the body (11) of the backpack (1) for domiciliary medical services; likewise on the part later (11.post) of same Body (11) of backpack (1) the load distribution system (30) has an adjustable belt (32) that has an adjustable strap (32.1) that in turn has two sections (32.1', 32.1") each of its respective ends are joined by thread seams to triangular tabs (11.6) that find united in the lower part in each of the sides (11der, 11left) of body (11) of the backpack (1) for domiciliary medical services; and finally on the same back (11.post) of the same body (11) of the backpack (1), the load distribution system (30) comprises a padded back support (33), this padded back support (33) is attached and assembled by means of thread seams to the outside of the PC pocket (19 b), whereas this padded back support (33) is adjacent to the rectangular wall (11.2) of the body (11), which is a reinforcement and structural support of weight in the backpack (1) and which, in turn, helps to support and balance all the forces due to the weight carried in the backpack (1) providing the user with greater comfort and support when carrying it (See FIGS. 2, 3, 4, 5, 15, 16, 20, 24, 25, 26, 27, 28, 29, 27, 28, 29, and 30).

The backpack (1) for domiciliary medical services comprises a methodology for its implementation, which is integrated to the medical home services as follows:

First contact with clients, calling the client, informing the new services included in his insurance policy.

The staff of Seguros Bolivar communicates with the client.

The patient receives a call from Seguros Bolivar to report on the medical service, once the details of the home consultation with the patient and with the health professional have been specified, said health professional, prepares his backpack (1) to visit the patients.

Preparation of backpack (1) the health professional saves his/her personal belongings in the respective separate space.

The health professional organizes all items, medical equipment and medical consumables in the different compartments, spaces or pockets predisposed in the removable compartment (17), then the removable compartment (17) is inserted inside the backpack (1).

The physician or health professional already has all his elements and is ready to go, he takes his backpack (1) and places it on his back, locating the two adjustable vertical straps (31) to distribute the weight properly and at the same time adjust the adjustable belt (32) on his waist to lighten the load and prevent the backpack (1) from bouncing on the back.

The doctor or health professional travels in his usual means of transportation (mass transportation).

The doctor or health professional enters in the massive transportation with the backpack (1) in the hands, locating the backpack (1) in a place that does not bother other passengers, protecting the backpack (1) to avoid discomfort.

The doctor or health professional arrives at the patient's House, it greets and recommends where the consultation should be done, before starting to diagnose the patient, start the hands hygiene protocol, choosing the ideal place to carry out the consultation, and at the same time placing the backpack (1) in such a way that both he and the patient can observe its contents.

The doctor or health professional will diagnose the patient, but before he cleans the instruments using the special cloths provided by the medical center, also using the antibacterial gel provided by the medical center, wash his hands before starting the diagnosis, putting on the gown to protect the patient.

The doctor examines the patient and after the diagnosis, discards the wastes of the consultation. The doctor opens the side pocket (20A) of the backpack (1) to take the waste container (20-one) to deposit the waste and the places such in the bag with snaps (24) and places such within the container (21) and within the side pocket (20 A) of backpack (1) isolating the waste from the backpack (1), so they do not come into contact with personal items, or others carried in the backpack (1).

The medical is ready to formulate, taking the forms of the backpack (1) and begins to formulate the patient.

BRIEF DESCRIPTION OF THE DRAWINGS

FIG. 1. Shows an isometric view of the backpack (1) for domiciliary medical services with all its features and assembly.

FIG. 1A. Shows an isometric of backpack (1) for domically medical services teaching its components such What a Main body (10), a base (20) and a load distribution system (30).

FIG. 2. Shows a top view, a front view, and a right-side view of the backpack (1) for domiciliary medical services teaching each of its components.

FIG. 3. Shows a right-side sectional view of the backpack (1) for domiciliary medical services, presenting the assembly with the removable compartment (17) and respective components or technical features.

FIG. 4. Shows an exploded view of the backpack (1) for domiciliary medical services presenting all its technical features and assembly.

FIG. 5. Sample view in explosion of the body (11) of the main body (10) of the backpack (1) for domiciliary medical services showing all its constructive technical characteristics.

FIG. 6. Shows a front view and a right-side view of the right-side pocket (12) of the body (11) of the backpack (1) for domiciliary medical services, showing all its constructive technical characteristics.

FIG. 7. Sample of frontal view and an explosion view of the left side pocket (13) of the body (11) of the backpack (1) for domiciliary medical services, showing all its constructive technical characteristics.

FIG. 8. Shows a top view of the upper handle (14) of the body (11) of the backpack (1) for domiciliary medical services teaching all their features techniques constructive.

FIG. 9. Shows a top view of the right-side handle (15) of the body (11) of the backpack (1) for domiciliary medical services showing all its technical characteristics constructive.

FIG. 10. Sample of top view of the upper anti-theft zipper (16) of body (11) of the backpack (1) for domiciliary medical services showing all its technical characteristics constructive.

FIG. 11. Shows a top view and two exploded views of the removable compartment (17) of the body (11) of the backpack (1) for domiciliary medical services, showing all its constructive technical characteristics.

FIG. 12. Shows a front view of the elastic interlaced woven panel (19) of the body (11) of the backpack (1) for domiciliary medical services, showing all its construction technical characteristics.

FIG. 13. Shows a front view of the mobile pocket (19 A) of the body (11) of the backpack (1) for domiciliary medical services showing all its construction technical characteristics.

FIG. 14. Shows a front view, two left side views of the large pocket (19 A.1) of the body (11) of the backpack (1) for domiciliary medical services showing all its technical characteristics constructive.

FIG. 15. Sample a view side right, a rear view of the PC pocket (19 B) of the body (11) of the backpack (1) for domiciliary medical services, showing all its technical characteristics constructive.

FIG. 16. Shows a right-side view of the side pockets (20 A, 20 B) of the body (11) of the backpack (1) for domiciliary medical services, showing all its technical characteristics constructive.

FIG. 17. Shows an explosive view of the waste container (21) showing all its technical characteristics.

FIG. 18. Shows an exploded view of the auxiliary side container (22) showing all its technical characteristics.

FIG. 19. Shows a top view of the safety zipper (23) of the body (11) of the backpack (1) for domiciliary medical services showing all its constructive technical characteristics.

FIG. 20. It shows a right-side view, a front view of a security bag with snaps (24) showing all its technical characteristics.

FIG. 21. Sample view of the adjustable vertical straps (31) showing all their technical and constructive characteristics.

FIG. 22. Sample view of a frontal of the adjustable belt (32) teaching all its technical characteristics.

FIG. 23. Shows an exploded view of the padded back support (33), showing all its technical characteristics.

FIG. 24. Shows four exploded views of the backpack (1) for domiciliary medical services with the B1 configuration, showing all its technical characteristics.

FIG. 25. Shows two exploded views of the backpack (1) for domiciliary medical services with the setting B1, teaching a side pocket (20 A), the waste container (21) and security bag with snaps (24).

FIG. 26. Shows a frontal view and rear view of backpack (1) and a view in explosive of removable compartment (17) of backpack (1) with the A1 configuration, showing all its technical characteristics and their respective assemble.

FIG. 27. Shows a front view and two left side views of the backpack (1) for domiciliary medical services with configuration A1, showing all its construction technical characteristics and its respective assembly.

FIG. 28. Shows a right side view, left side view, a rear view and a detail view of the backpack (1) for domiciliary medical services with the A1 configuration, showing all its construction and technical characteristics and assemble.

FIG. 29. Shows the backpack (1) for domiciliary medical services A1 configuration, showing all its constructive technical characteristics and its respective assembly.

FIG. 30 Shows the backpack (1) for domiciliary medical services with the A1 configuration, showing the assembly of the removable compartment (17) together with all its construction technical characteristics and its respective assembly.

FIG. 31 Shows an exploded view of the support or stud (18), showing all its construction technical characteristics.

SUMMARY OF THE INVENTION

This Patent application refers to a backpack for domiciliary medical services, to optimize the transport, protection, cleaning and organization of basic medical elements (equipment and consumables) when used in patient care in each domiciliary or home visit and medical consultation by the doctor or health professional, likewise this backpack for domiciliary medical services allows easy access to medical items and personal items carried, it also provides versatility in adjustment and adaptation in each of its interior spaces according to the needs of the health care professional, in addition this backpack facilitates the cleaning and disinfection of all its inside elements by means of oxygen, UV light, water, soap, ammonium, among others, against microorganisms and bacteria that can impregnate or adhere to it. A backpack is provided for domiciliary medical services which allows a safe and effective disposal of any waste and/or hazardous waste used in the medical consultation such as syringes, gauze, tongue depressors, bandages, band-aids, etc., likewise this backpack provides to lighten the load and avoid unwanted rebounds on the back of the health professionals, which minimizes the risk of damage caused to his spine and shoulders, also this backpack simplifies its transport in confined or reduced spaces such as in public transport, avoiding disturbing other passengers or people, as it is easy to locate on the ground, on the chest or positioned laterally to one side of the health professional who carries it, in addition this bag has safety measures for its opening and, in turn, is designed in such a way that it can be unnoticed to possible threats or crime attacks when moving from one place to another or within the same mass transportation system. The backpack for domiciliary medical services allows to separate and isolate the personal objects of the physician or health professional with respect to the basic medical elements (equipment and consumables), likewise this backpack guarantees order and organization of both the basic medical elements (equipment and consumables) and of the personal elements of the doctor or health professional, allowing the disposition any of these contents by accessing and easily detecting said elements in an agile and fast way.

The invention claimed is:

1. A backpack (1) for domiciliary medical services, comprising:
- a main body (10) including a front wall (11.1), a rear wall (11.2), a bottom wall (11.3), and left and right openings (11.4, 11.5);
- a first elongated tab (11.6) inside the right opening along at least part of the perimeter of the right opening and a second elongated tab (11.7) positioned inside the right opening vertically along the rear wall (11.2);
- a plurality of first snaps (11.6.1, 11.7.1) on the first and second elongated tabs;
- a divider wall (11.8) within the main body having a hook and loop attachment band (11.8.1) thereon;
- a right side pocket (12) with an outer cover (12.1), a handle (15), and a zipper (16) between the cover and the main body;
- a left side pocket (13) with an outer cover (13.1) and a zipper (16) between the cover and the main body;
- a left side accessory pocket (13.1.1) located on the cover of the left side pocket;
- an upper handle (14) including an elongated body (14.1) and a reinforcing sheath (14.2);
- a removable compartment (17) sized and shaped to fit within the right opening (11.5) and including a plurality of divider panels (17.3.1, 17.3.2, 17.4.1, 17.4.2), a plurality of second snaps (17.2.3.1) that mate with the first snaps of the first and second elongated tabs, a hook and loop fastener (17.3) that mates with the hook and loop attachment band of the divider wall, and a handle (17.5.1);
- a panel (19) including a plurality of elastic bands (19.1.2, 19.1.3) woven together, wherein the panel can be removably attached to the removable compartment (17);
- at least one cell phone pocket (19A) located within the main body (10) and secured to the rear wall (11.2);
- a PC pocket (19B) located on the outside of the main body (10), secured to the rear wall (11.2), and including internal pockets (19B.2, 19B.3) therein;
- a base (20) attached beneath the main body including a left side base pocket (20A) and a right side base pocket (20B);
- a waste container (21) configured to be received in one of the base pockets and including a lining (21.2) with lining snaps (21.2.1);
- a lined auxiliary container (22) configured to be received in another of the base pockets;
- a security bag (24) with security bag snaps (24.2.1) that mate with the lining snaps (21.2.1);
- a load distribution system (30) including at least one vertical shoulder strap (31) with a card holder pocket (31.2) and an adjustable strap (31.4) with a fastener (31.5);
- and a padded back support (33).

2. The backpack (1) for domiciliary medical services, according to claim 1, wherein the right side base pocket (20B), the waste container (21), and the security bag (24) are provided on a right lateral side (11.right) of a body (11) of the backpack (1).

3. The backpack (1) for domiciliary medical services, according to claim 1, wherein the removable compartment (17), the panel (19), the PC pocket (19B), the left side base pocket (20 A), the right side base pocket (20 B), the upper handle (14), and the right side pocket handle (15) are made of a polyester textile material; the zipper (16) and a safety zipper (23) are made of a polyester textile material and at least one of steel, bronze or brass material; and the security bag (24) is made of polyethylene, PVC, PVDC, or polyester textile material.

4. The backpack (1) for domiciliary medical services, according to claim 1, wherein the backpack (1) is assembled at its base (20) by one of seams, rivets or heat to four supports or studs (18) located equidistantly on the base (20).

5. The backpack (1) for domiciliary medical services, according to claim 1, wherein the panel (19) is located internally within a special pocket (17.5) of the removable compartment (17).

6. The backpack (1) for domiciliary medical services, according to claim 1, wherein the left side base pocket (20A) is attached to a side wall (11.3.1) that forms a base of a body (11) of the main body (10).

7. The backpack (1) for domiciliary medical services, according to claim 1, wherein the padded back support (33) is arranged inside and adjacent to the rear wall (11.2) of a body (11) of the backpack (1).

8. The backpack (1) for domiciliary medical services, according to claim 1, wherein the right side base pocket (20B) and the left side base pocket (20A) have the same structural configuration.

9. The backpack (1) for domiciliary medical services, according to claim 8, wherein the right side base pocket (20B) is adjacent to the left side base pocket (20A).

10. The backpack (1) for domiciliary medical services, according to claim 1, wherein the left side base pocket (20A), and the lined auxiliary side container (22) are provided on a left lateral side (11.left) of a body (11) of the backpack (1).

* * * * *